US009796770B2

(12) United States Patent
Mintz et al.

(10) Patent No.: US 9,796,770 B2
(45) Date of Patent: Oct. 24, 2017

(54) IMMUNOGLOBULIN REDUCED IN THROMBOGENIC AGENTS AND PREPARATION THEREOF

(71) Applicant: Omrix Biopharmaceuticals Ltd., Rehovot (IL)

(72) Inventors: Roni Mintz, Moshav Shafir (IL); Oleg Belyaev, Barnaul (RU); Israel Nur, Moshav Timmorim (IL); Liliana Bar, Rehovot (IL); Roberto Meidler, Rehovot (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 39 days.

(21) Appl. No.: 14/678,319

(22) Filed: Apr. 3, 2015

(65) Prior Publication Data

US 2015/0210754 A1 Jul. 30, 2015

Related U.S. Application Data

(62) Division of application No. 13/470,788, filed on May 14, 2012, now Pat. No. 9,023,994.

(60) Provisional application No. 61/550,581, filed on Oct. 24, 2011, provisional application No. 61/486,386, filed on May 16, 2011.

(30) Foreign Application Priority Data

May 16, 2011 (IL) .......................... 212911

(51) Int. Cl.
| | |
|---|---|
| C07K 1/18 | (2006.01) |
| A61K 39/395 | (2006.01) |
| C07K 16/06 | (2006.01) |
| A61K 39/00 | (2006.01) |

(52) U.S. Cl.
CPC ...... *C07K 16/065* (2013.01); *A61K 39/39591* (2013.01); *C07K 1/18* (2013.01); *A61K 2039/505* (2013.01); *C07K 2317/10* (2013.01); *Y10S 530/83* (2013.01); *Y10S 530/831* (2013.01)

(58) Field of Classification Search
CPC ...... C07K 16/065; C07K 1/18; C07K 16/165; C07K 2317/10; C07K 1/16; C07K 1/14; A61K 39/39591; A61K 35/16; Y10S 530/83; Y10S 530/831; B01D 15/362; B01D 15/363; B01D 15/424; B01D 15/327

See application file for complete search history.

(56) References Cited

U.S. PATENT DOCUMENTS

| | | |
|---|---|---|
| 4,272,521 A | 6/1981 | Zuffi |
| 4,296,027 A | 10/1981 | Condie |
| 5,164,487 A | 11/1992 | Kothe et al. |
| 5,252,217 A | 10/1993 | Burnouf-Radosevich et al. |
| 6,281,336 B1 | 8/2001 | Laursen et al. |
| 6,468,733 B2 | 10/2002 | Nur et al. |
| 6,592,905 B1 | 7/2003 | Ayers et al. |
| 7,138,120 B2 | 11/2006 | Laursen et al. |
| 8,304,524 B2 * | 11/2012 | Bairstow ............ A61K 38/1709 530/380 |
| 2006/0194953 A1 | 8/2006 | Bonnerjea et al. |
| 2008/0014625 A1 | 1/2008 | Etzel |
| 2008/0193981 A1 | 8/2008 | Fahrner et al. |
| 2010/0311952 A1 | 12/2010 | Falkenstein et al. |

FOREIGN PATENT DOCUMENTS

| | | |
|---|---|---|
| EP | 1161958 | 6/2007 |
| JP | 6-107561 | 4/1994 |
| JP | 2010-528076 | 8/2010 |
| JP | 2013-540787 | 11/2013 |
| JP | 56-16416 | 10/2014 |
| RU | 2197500 | 1/2003 |
| WO | WO 99/18130 | 4/1999 |
| WO | WO 99/33484 | 7/1999 |
| WO | WO 99/64462 | 12/1999 |
| WO | WO03/078454 * | 9/2003 |
| WO | WO 2007/017859 | 2/2007 |
| WO | WO2007/046631 * | 4/2007 |
| WO | WO 2008/145351 | 12/2008 |
| WO | WO 2010/072381 | 7/2010 |
| WO | WO 2012/059308 | 5/2012 |

OTHER PUBLICATIONS

Alving, B.M. et al 'Contact-activated factors: contaminants of immunoglobulin preparations with coagulant and vasoactive properties' J Lab Clin Med (1980) vol. 96, No. 2 pp. 334-346.
Bouma, B.N. et al 'Human Blood Coagulation Factor XI: Purification, Properties, and Mechanism of Activation by Activated Factor XII' J. Biol. Chem. (1977) vol. 252, No. 18 pp. 6432-6437.
Brannagan, III T.H. et al 'Complications of intravenous immune globulin treatment in neurologic disease' Neurology (1996) vol. 47 pp. 674-677.
Buchacher, A. et al 'Purification of intravenous immunoglobulin G from human plasma—aspects of yield and virus safety' Biotechnology Journal (2006) vol. 1 No. 2 pp. 148-163.
Dalakas MC. 'High-dose intravenous immunoglobulin and serum viscosity: Risk of precipitating thromboembolic events' Neurology (1994) vol. 44 pp. 223-226.
Guerrier L et al. Specific sorbent to remove solvent-detergent mixtures from virus-inactivated biological fluids J. Chromatogr. B Biomed Appl. (1995) vol. 664, No. 1 pp. 119-125.
Jose, M. et al. 'Pasteurization Inactivates Clotting Enzymes During Flebogamma? and Flebogamma? Dif Production' Webmed Central Immunotherapy (2010) vol. 1 12 pages.
Protein liquid chromatography, Edited by Michael Kastner, Elsevier science B.V. 2000, pp. 45-49.
Reinhart W.H. et al 'Effect of high-dose intravenous immunoglobulin therapy on blood rheology' Lancet (1992) vol. 339 pp. 662-664.
Rosenbaum JT. 'Myocardial infarction as a complication of immunoglobulin therapy' Arthritis Rheum (1997) vol. 40 pp. 1732-1733.
Siegel, J. The Product: All Intravenous Immunoglobulins Are Not Equivalent. The Journal of Human Pharmacology and Drug Therapy (2005) vol. 25, No. 11 Part 2, pp. 78S-84S.

(Continued)

*Primary Examiner* — Phuong Huynh
(74) *Attorney, Agent, or Firm* — David R. Crichton

(57) ABSTRACT

The invention relates to an immunoglobulin composition reduced in thrombogenic agents and to methods for its preparation. One method comprises subjecting an immunoglobulin containing solution to a negative cation exchanger chromatography at a pH in the range of higher than 3.8 to equal to or lower than 5.3. The solution can also be subjected to a negative anion exchanger chromatography at a pH in the range of 7 to 8.2.

22 Claims, No Drawings

(56) References Cited

OTHER PUBLICATIONS

Teschner, W. et al 'A new liquid, intravenous immunoglobulin product (IGIV 10%) highly purified by a state-of-the art process' (2007) Vox Sanguinis vol. 92, No. 1 pp. 42-55.
Wessler, S. et al. 'Biologic assay of a thrombosis-inducing activity in human serum' J Appl Physiol. (1959) vol. 14, No. 6 pp. 943-946.
Wolberg, A.S. et al 'Coagulation Factor XI is a Contaminant in Intravenous Immunoglobulin Preparations' Am J Hem (2000) vol. 65 pp. 30-34.
Cohn, E.J. The history of plasma fractionation. In Advances in Military Medicine, Andrus et al. Eds. Little, Brown & Co, 1948.
Practical Protein Chromatography edited by Kenney and Fowell vol. 11 Humana Press, 1992.
Hermanson et al Immobilized Affinity Ligand Techniques (Academic Press Inc. 1992).
International Search Report re: PCT/IL2012/000189 dated Jan. 11, 2013.
International Preliminary Report on Patentability re: PCT/IL2012/000189 dated Nov. 19, 2013.
Horenstein A. L. et al. "Purification of clinical-grade monoclonal antibodies by chromatographic methods", Therapeutic Proteins: Methods and Protocols (2005) p. I91-208.

* cited by examiner

IMMUNOGLOBULIN REDUCED IN THROMBOGENIC AGENTS AND PREPARATION THEREOF

CROSS-REFERENCE TO RELATED APPLICATIONS

This application is a divisional that claims the benefit of U.S. application Ser. No. 13/470788, filed on May 14, 2102, which claims priority from U.S. Provisional Application No. 61/550581, filed on Oct. 24, 2011, and U.S. Provisional Application No. 61/486386, filed on May 16, 2011, and from Israel Patent Application No. 212911, filed on May 16, 2011. The complete disclosures of the aforementioned related U.S. patent applications are hereby incorporated herein by reference for all purposes.

FIELD OF THE INVENTION

The invention relates to an immunoglobulin preparation comprising low levels of thrombogenic agents.

BACKGROUND OF THE INVENTION

Intravenous immunoglobulin (IVIG) preparations are increasingly used for the treatment of a variety of immunological deficiencies and autoimmune disorders including dermatomyositis, idiopathic thrombocytopenic purpura, Kawasaki disease, and Guillain-Barré syndrome. A small number of thromboembolic adverse events have been associated with the use of WIG preparations (Brannagan et al. Complications of intravenous immune globulin treatment in neurologic disease. Neurology 1996; 47:674-677; Rosenbaum J T. Myocardial infarction as a complication of immunoglobulin therapy. Arthritis Rheum 1997; 40:1732-1733; and Dalakas M C. High-dose intravenous immunoglobulin and serum viscosity: risk of precipitating thromboembolic events. Neurology 1994; 44:223-226).

These events, which include deep venous thrombosis and myocardial infarction, have primarily been observed in patients receiving high-dose WIG, and they have been attributed to an increase in blood viscosity (Dalakas M C. 1994; and Reinhart W H, Berchtold P E. Effect of high-dose intravenous immunoglobulin therapy on blood rheology. Lancet 1992; 339:662-664).

Components of the contact system of blood coagulation have previously been identified in human immunoglobulin preparations (Alving et al. Contact-activated factors: contaminants of immunoglobulin preparations with coagulant and vasoactive properties. J Lab Clin Med 1980; 96:334-346). Commercial preparations of immune serum globulin were shown to contain widely varying levels of prekallikrein activator (PKA) and kallikrein activity. These activities were of interest because of their potential to produce bioactive peptides that can increase vascular permeability. The presence of vasoactive fragments of these proteins was thought to be related to occasional adverse reactions during administration of immunoglobulin preparations. These authors also found factor XI (FXI) in immunoglobulin preparations (Alving et al. 1980).

In Alving et al. (1980) twenty-five lots of commercial Imune Serum Globulins (ISG) were analyzed for PKA and kallikrein, components of the contact activation system, which could mediate such reactions through the generation of kinins in recipients. Kallikrein activity ranged from undetectable levels to >60% of the total potential kallikrein activity in normal plasma. PKA ranged from 5% to 3950% of the activity in a reference plasma protein fraction that had caused hypotension. All but five lots increased vascular permeability in the guinea pig. The five lots which caused no increase were also the lowest in PKA and kallikrein activity. When the immunoglobulin preparation was subjected to gel chromatography to separate the enzymatic contaminants from immunoglobulin G, only the fractions containing PKA and/or kallikrein increased vascular permeability. Several lots of IVIG shortened the nonactivated partial thromboplastin time of normal plasma from 236 seconds to 38 to 55 seconds. During gel chromatography, coagulant activity was eluted in a position corresponding to a molecular weight of 150,000; which was inhibited by antibody to human factor XI. These data indicate that factor XIa is responsible for the procoagulant activity observed and that PKA and/or kallikrein are potential mediators of vasoactive reactions to IVIG preparation.

Immunoglobins have also been found to contaminate factor XI preparations. Factor XI and immunoglobulins co-purify through successive ion-exchange columns and require the addition of a specific concanavalin A affinity chromatography column to remove traces of IgG contamination from factor XI (Bonno B N, Griffin J H. Human blood coagulation factor XI: purification, properties, and mechanism of activation by activated factor XII. J Biol Chem 1977; 252:6432-6437).

Wolberg et al. (Coagulation Factor XI Is a Contaminant in Intravenous Immunoglobulin Preparations. Am J Hem 2000; 65:30-34) demonstrated that a procoagulant, identified as activated factor XI, is present in IgG preparations. In this study, twenty-nine samples of intravenous immunoglobulin (IVIG) from eight different manufacturers were assayed for procoagulant activity. Twenty-six of these samples shortened the clotting time of factor XI-deficient plasma. Of these, fourteen samples had factor XI activities greater than 0.001 U/ml of normal pooled plasma. The remaining samples possessed less than 0.001 U/ml of normal plasma activity. The procoagulant activity in these samples could be inhibited by an anti-factor XI polyclonal antibody, suggesting that the procoagulant activity was factor XI. The procoagulant activity increased in two samples after storage at 4° C. for 4 weeks, likely as a result of factor XIa autoactivation. Additionally, activity in some IVIG samples was able to directly activate factor IX, indicating that activated factor XI was present in these samples.

During the last 3 centuries numerous methods for purification of intravenous immunoglobulin has been developed to meet the growing demand for IVIG. The vast majority of the manufacturing process includes various technologies for capturing the immunoglobulin on a dedicated resin usually an ion exchange resin (Jerry Siegel. The Product: All Intravenous Immunoglobulins Are Not Equivalent. The Journal of Human Pharmacology and Drug Therapy. Volume 25, Issue 11 Part 2, November 2005). Capturing of immunoglobulin on a resin is very expensive and time consuming since it requires a large amount of resin. In average, every liter of ion exchange resin captures about 30-50 g immunoglobulin. Therefore, when using a conventional large column with a capacity of about 100 L resin, 3-5 Kg immunoglobulin can be captured. Capturing the agents present in the immunoglobulin solution by a small column has an economical benefit.

U.S. Pat. No. 5,252,217 discloses a human Factor XI concentrate prepared by applying a cryoprecipitated plasma supernatant to a filtration-adsorption step and a single step of chromatography on cation exchange resin. The concentrate obtained is perfectly suitable for therapeutic use in replacement therapy in cases of Factor XI deficiency. The cation exchange resin is equilibrated with a buffer solution at a pH of 5.5 to 6.5, and preferably a pH of 6.

U.S. Pat. No. 4,272,521 discloses a method for the removal of both prekallikrein activator (PKA) and kallikrein-activatable precursor to PKA (Factor XII) from an immune serum globulin (ISG) solution using an ion exchange material at a pH of 27.2.

U.S. Pat. No. 5,164,487 discloses a method of manufacturing an intravenously tolerable immunoglobulin-G preparation that is free of aggregates, vasoactive substances and proteolytic enzymes. The starting material is treated with 0.4 to 1.5% by volume of octanoic acid and then chromatographed, especially on an ion or cation exchanger or hydrophobic matrix.

United States Patent Application 2010/0311952 discloses a method for purifying an immunoglobulin, wherein the method comprises applying an aqueous, buffered solution comprising an immunoglobulin in monomeric and in aggregated form to a cation exchange material under conditions whereby the immunoglobulin in monomeric form does not bind to the cation exchange material, and recovering the immunoglobulin in monomeric form from the solution after the contact with the cation exchange material.

PCT application WO2010/072381 discloses a method for purifying an immunoglobulin, wherein the method comprises applying an aqueous, buffered solution comprising an immunoglobulin in monomeric, in aggregated, and in fragmented form to an anion exchange chromatography material under conditions whereby the immunoglobulin in monomeric form does not bind to the anion exchange material, and recovering the immunoglobulin in monomeric form in the flow-through from the anion exchange chromatography material, whereby the buffered aqueous solution has a pH value of from 8.0 to 8.5. In one embodiment the anion exchange chromatography material is a membrane anion exchange chromatography material.

Jose et al. (2010) discloses that pasteurization during Immune Globulin Intravenous production inactivates some thrombogenic agents such as clotting enzymes. However, this method does not selectively inactivate the clotting enzymes and thus may alter the activity of the immunoglobulin solution.

Thus, there is a need for a method which selectively removes thrombogenic agent from an immunoglobulin solution without affecting the immunoglobulins.

SUMMARY OF THE INVENTION

The present invention relates to a method for specifically removing PKA, kallikrein and/or FXI(a) from an immunoglobulin preparation. In one embodiment, the immunoglobulin preparation is derived from a blood or blood fraction.

In one aspect, the invention provides a method for removing a thrombogenic agent from an immunoglobulin containing solution, the method comprising the steps of: providing the immunoglobulin containing solution at a pH in the range of higher than 3.8 to equal to or lower than 5.3; providing a support comprising immobilized negatively charged groups; contacting the solution with the support; and collecting an unbound fraction I.

In one embodiment of the present invention, the solution has a pH in the range of higher than 3.8 to equal to or lower than 5.0.

In another embodiment of the present invention, the solution has a pH in the range of equal to or higher than 4.0 to equal to or lower than 5.0.

In another further embodiment of the present invention, the solution has a pH in the range of higher than 3.8 to equal to or lower than 4.7.

Yet in another embodiment of the invention, the solution has a pH of about 4.0, 4.1, 4.2, 4.3, 4.4, 4.5, 4.6, or 4.7.

Yet in another further embodiment of the invention, the solution has a pH in the range of higher than 3.8 to equal to or lower than 4.3.

In another embodiment of the invention, the solution has a pH in the range of equal to or higher than 4.0 to equal to or lower than 4.3.

In another further embodiment of the invention, the solution has a pH in the range of equal to or higher than 4.1 to equal to or lower than 4.3.

In one embodiment of the present invention, the unbound fraction I is further contacted with the support comprising the immobilized negatively charged groups under the same pH; and an unbound fraction II is collected.

In another embodiment of the present invention, the support is in the form of a chromatographic material or a chromatographic membrane.

In another embodiment of the present invention, the support material or membrane is hydrophilic and selected from the group consisting of agarose, sepharose, acrylic beads, cellulose, controlled pore glass, silica gels, and dextrans; hydrophobic and selected from the group consisting of resins; or organic synthetic polymer selected from the group consisting of materials or membranes based on polyacrylamides or polystyrens.

In one embodiment of the present invention, the negatively charged groups are immobilized to the support via a linker present between the support and the negatively charged groups.

In one embodiment of the present invention, the linker is selected from the group consisting of a protein, amino acid and peptide.

In one embodiment of the present invention, the support is chemically modified.

In one embodiment of the present invention, the support is a weak or a strong cation exchanger.

In one embodiment of the present invention, the immobilized negatively charged groups are selected from the group consisting of derivatives of sulfonic and other sulfur containing acids, formic and other carboxylic acids, phosphoric and other phosphorous containing acids, nitrate and other nitrogen containing acids, and a combination thereof.

In one embodiment of the present invention, the immobilized negatively charged groups are sulfur containing acids such as sulfopropyl.

In one embodiment of the present invention, the immobilized negatively charged groups are carboxylic acids such as carboxymethyl.

In one embodiment of the present invention, the method further comprises the steps of: adjusting the unbound fraction I or the unbound fraction II to a pH in the range of 7 to 8.2; contacting the unbound fraction I or the unbound fraction II with a support comprising immobilized positively charged groups at a pH in the range of 7 to 8.2; and collecting an unbound fraction.

In one embodiment of the present invention, the method further comprises the steps of adjusting and contacting the solution, prior to contacting with the support comprising immobilized negatively charged groups, with a support comprising immobilized positively charged groups at a pH in the range of 7 to 8.2; and collecting an unbound fraction.

In one embodiment of the present invention, the immobilized positively charged groups are selected from the group consisting of ammonium, alkyl ammonium, dialkylammonium, trialkyl ammonium, quaternary ammonium, alkyl groups, $H^+$, $Na^+$, $K^+$, $Ca^{2+}$, $Mg^{2+}$, amino functional group, and a combination thereof.

In one embodiment of the present invention, the immobilized positively charged groups are quaternary ammonium. The quaternary ammonium can be Diethylaminoethyl (DEAE).

Still in another embodiment of the invention, the method comprises contacting the solution with the support comprising the immobilized positively charged groups at a pH in the range of 7 to 8.2; collecting the unbound fraction; adjusting the pH of the unbound fraction to a pH in the range of higher than 3.8 to equal to or lower than 5.3; contacting the unbound fraction with the support comprising the immobilized negatively charged groups at a pH in the range of higher than 3.8 to equal to or lower than 5.3; and collecting the unbound fraction I.

Still in another further embodiment of the invention, the adjusting and contacting the unbound fraction with the support comprising the immobilized negatively charged groups is carried out at a pH in the range of higher than 3.8 to equal to or lower than 5.0.

In one embodiment of the present invention, the adjusting and contacting the unbound fraction with the support comprising the immobilized negatively charged groups is carried out at a pH in the range of equal to or higher than 4.0 to equal to or lower than 5.0.

In one embodiment of the present invention, the adjusting and contacting the unbound fraction with the support comprising the immobilized negatively charged groups is carried out at a pH in the range of higher than 3.8 to equal to or lower than 4.7.

In one embodiment of the present invention, the adjusting and contacting the unbound fraction with the support comprising the immobilized negatively charged groups is carried out at a pH of about 4.0, 4.1, 4.2, 4.3, 4.4, 4.5, 4.6, or 4.7

In one embodiment of the present invention, the adjusting and contacting the unbound fraction with the support comprising the immobilized negatively charged groups is carried out at a pH in the range of higher than 3.8 to equal to or lower than 4.3.

In one embodiment of the present invention, the adjusting and contacting the unbound fraction with the support comprising the immobilized negatively charged groups is carried out at a pH in the range of equal to or higher than 4.0 to equal to or lower than 4.3.

In one embodiment of the present invention, the adjusting and contacting the unbound fraction with the support comprising the immobilized negatively charged groups is carried out at a pH in the range of equal to or higher than 4.1 to equal to or lower than 4.3.

In another embodiment of the present invention, contacting the solution with the support comprising the positively charged groups is carried out at a linear velocity in the range of 1 to 2 ml/min/cm², and the immunoglobulin containing solution has a temperature in the range of 8 to 37° C.

In one embodiment of the present invention, the method further comprises the steps of: contacting the solution prior to contacting with the support comprising immobilized negatively charged groups with a chromatographic material comprising three-dimensional cross-linked hydrophobic acrylic polymer; and collecting an unbound fraction III.

In one embodiment of the present invention, the method further comprises the steps of: contacting the unbound fraction, unbound fraction I or unbound fraction II with a chromatographic material comprising three-dimensional cross-linked hydrophobic acrylic polymer, and collecting an unbound fraction III.

In one embodiment of the present invention, the support comprising immobilized positively charged groups is a weak or a strong anion exchanger.

Another aspect of the invention relates to a method for preparing an immunoglobulin composition comprising the steps of: subjecting an immunoglobulin containing solution to at least two steps of negative chromatography: an anion exchanger chromatography at a pH in the range of 7 to 8.2; followed by a cation exchanger chromatography at a pH in the range of higher than 3.8 to equal to or lower than 5.3.

In one embodiment of the present invention, the cation exchanger chromatography is carried out twice. In one embodiment, the two cation exchanger chromatography are carried out in tandem.

In one embodiment of the present invention, the cation exchanger chromatography is carried out at a pH in the range of higher than 3.8 to equal to or lower than 5.0.

In another embodiment of the present invention, the cation exchanger chromatography is carried out at a pH in the range of equal to or higher than 4.0 to equal to or lower than 5.0.

In another further embodiment of the present invention, the cation exchanger chromatography is carried out at a pH in the range of higher than 3.8 to equal to or lower than 4.7.

Yet in another embodiment of the present invention, the cation exchanger chromatography is carried out at a pH of about 4.0, 4.1, 4.2, 4.3, 4.4, 4.5, 4.6, or 4.7.

Yet in another further embodiment of the present invention, the cation exchanger chromatography is carried out at a pH in the range of higher than 3.8 to equal to or lower than 4.3.

Still in another embodiment of the present invention, the cation exchanger chromatography is carried out at a pH in the range of equal to or higher than 4.0 to equal to or lower than 4.3.

Still in another further embodiment of the present invention, the cation exchanger chromatography is carried out at a pH in the range of equal to or higher than 4.1 to equal to or lower than 4.3.

In one embodiment of the present invention, the method further comprises a negative chromatography using a chromatographic material comprising three-dimensional cross-linked hydrophobic acrylic polymer.

In one embodiment of the present invention, the cation exchanger is in the form of a membrane.

In one embodiment of the present invention, the cation exchanger comprises a sulfonic functional group.

In another aspect, the invention relates to an immunoglobulin composition derived from blood or blood fractions, comprising 4%-10% protein and obtainable according to the method of the invention.

The invention also provides a receptacle containing the immunoglobulin composition according to the invention.

In another aspect, the invention provides a method for treating a subject suffering from an immunodeficiency, an inflammatory disease, an autoimmune disease, or an acute infection, comprising administering to the subject an effective amount of an immunoglobulin composition according to the invention.

DESCRIPTION OF THE EMBODIMENTS OF THE INVENTION

The invention relates to a method for removing thrombogenic agents from an immunoglobulin preparation. In one embodiment of the invention, the immunoglobulin preparation is derived from blood or blood fractions. In another embodiment, the blood or blood fractions are from more than one donor or from a plurality of donors.

It was found according to the present invention that FXI and/or its active form FXIa can be effectively removed from an immunoglobulin containing solution by subjecting the immunoglobulin solution to a cation exchanger chromatography at a pH level of lower than 6. Optimal results were obtained in a pH range of higher than 3.8 to equal to or lower than 5.3. This pH range was found to effectively remove FXIa and at the same time substantially preserve the immunoglobulin (IgG) levels.

These findings are surprising, in view that the immunoglobulin (having an isoelectric point of 6-8 U.S. Pat. Nos. 6,592,905 and 4,296,027) has a positive net electrical charge at a pH level of lower than 6 and as such was expected to bind to the cation exchanger as well, thereby resulting in low immunoglobulin levels remaining in the solution (U.S. Pat. No. 6,592,905).

Without being bound by the mechanism, it appears that at a pH of lower than 6 FXIa and immunoglobulin compete for the negatively charged groups on the cation exchanger and binding of FXIa is more favorable.

Also, it was surprisingly found according to the present invention that a higher efficiency of FXIa removal from the immunoglobulin containing solution can be achieved by subjecting the immunoglobulin solution to the cation exchanger at a pH range of 4.0 to 4.3. These findings are also surprising due to the fact that FXIa has a positive net charge in a wide pH range and up to about pH 9 (its isoelectric point is 8.9-9.1; Haematologic Technologies Inc. Research Reagent Catalog). Surprisingly, these results were obtained either with a weak cation exchanger or with a strong cation exchanger.

It was also found according to the present invention that kallikrein (having an isoelectric point of 8.6-9.5) can be effectively removed from an immunoglobulin containing solution by subjecting the solution to a cation exchanger chromatography at a pH level of 4.1-4.3 while substantially preserving the IgG levels. These findings are surprising in light of that the immunoglobulin has a positive net electrical charge at this pH range and thus would have been expected to bind to the cation exchanger as well resulting in low immunoglobulin levels remaining in the solution.

The results show maximal removal of a thrombogenic agent from an IgG containing solution, by subjecting the solution to a cation exchanger under a very narrow pH range, while maintaining an unaltered level of immunoglobulin in the solution.

These findings paved the way to the development of a method for removing a thrombogenic agent from an immunoglobulin containing solution while preserving the majority of the immunoglobulin within the solution and/or without altering the IgG subclass distribution (e.g. IgG1—about 65%, IgG2—about 30%, IgG3—about 6%, and IgG4—about 1%). By "preserving the majority of the immunoglobulin within the solution" it is meant that the method allows a recovery of equal or more than 75% of the immunoglobulin as compared to the initial immunoglobulin content before contacting the solution with the support according to the invention. In one embodiment, the method allows a recovery of 80%, 85%, 90%, 95% and 99% of the immunoglobulin as compared to the initial immunoglobulin content before contacting the solution with the support according to the invention.

The invention provides a method for removing a thrombogenic agent from an immunoglobulin containing solution, the method comprising the steps of: providing the immunoglobulin solution at a pH in the range of higher than 3.8 to equal to or lower than 5.3; providing a support comprising immobilized negatively charged groups; contacting the solution with the support; and collecting an unbound fraction. In one embodiment of the invention, the solution has a pH in the range of higher than 3.8 to equal to or lower than 5.0. In another embodiment of the invention, the range is equal to or higher than 4.0 to equal to or lower than 5.0. In a further embodiment, the range is higher than 3.8 to equal to or lower than 4.7, such a pH of about 4.0, 4.1, 4.2, 4.3, 4.4, 4.5, 4.6, or 4.7. Yet, in a further embodiment, the range is higher than 3.8 to equal to or lower than 4.3. Yet, in a further embodiment, the range is equal to or higher than 4.0 to equal to or lower than 5.3. In another further embodiment, the range is very narrow, of equal to or higher than 4.0 to equal to or lower than 4.3 or about 4.1 to about 4.3 and specifically allows removal of FXIa and Kallikrein.

The term "thrombogenic agent" refers to an agent that has the potential to induce fibrin clot formation. The term "thrombogenic agent" is used herein interchangeably with the terms hemostatic, thrombotic and pro-coagulant agent. Thrombogenic agent may be, for example, kallikrein, FXI, FXIa, Factor XII, thrombin and PKA. The term "thrombogenic agent" includes thrombogenic induced agents and "thrombosis-generating agents" such as agents that activate thrombogenic factors in the coagulation cascade.

The term "support" as used herein includes a carrier, or any matrix used to attach, immobilize, carry, or stabilize the negatively charged groups. Supports are well known in the art as described in Hermanson et al. Immobilized Affinity Ligand Techniques (Academic Press Inc. 1992). The support for carrying out the method of the invention can be made of any material which is capable of binding a molecule comprising negatively charged groups. Solid supports include, but are not limited to, matrices, columns, coverslips, chromatographic materials, filters, microscope slides, test tubes, vials, bottles, ELISA supports, glass or plastic surfaces, chromatographic membranes, sheets, particles, beads, including magnetic beads, gels, powders, fibers, and the like.

In one embodiment of the invention the support is in the form of a chromatographic material. In another embodiment of the invention, the support is in the form of a chromatographic membrane. The support can be composed of a hydrophilic material such as agarose, sepharose, acrylic beads, cellulose, controlled pore glass, silica gels, dextranes; hydrophobic material such as resins; or an organic artificial/synthetic polymer such as materials based on polyacrylamides or polystyrens. Typical materials/polymers are commercially available under the trade names Sephacryl® (Pharmacia, Sweden), Ultragel® (Biosepara, France) TSK-Gel Toyopearl® (Toso Corp., Japan), HEMA (Alltech Ass. (Deer-field, Ill., USA), Eupergit® (Rohm Pharma, Darmstadt, Germany). Also materials based on azlactones (3M, St. Paul, Minn., USA). Particularly preferred is Agarose® or Sepharose®. These materials are commercially available, for example, from Sigma, St. Louis. The chromatographic material can be suspended in an appropriate medium and the resulting slurry can be used e.g. in a chromatographic column. However, the method of the invention can also be carried out batch-wise e.g. by using a test tube or a batch reactor. In one embodiment of the invention the support is a FRACTOGEL® EMD, a TOYOPEARL®, or a TSK-GEL® polymer matrix. Column chromatography is known in the art (Practical Protein Chromatography edited by Kenney and Fowell Volume 11 Humana Press, 1992) and generally refers to a technique in which a solution (the mobile phase) is allowed to travel down a column and an individual component is being adsorbed by the stationary phase e.g. by the chromatographic material. The term "negatively charged groups" refers to a molecule comprising chemical groups which carry a negative charge such as derivatives of sulfonic and other sulfur containing acids (e.g. $SO_4^{2-}$ and $SO_3^-$), formic and other carboxylic acids (e.g. $COO^-$), as well as phosphoric and other phosphorous containing acids (e.g. $PO_4^{3-}$), nitrate and other nitrogen containing acids(e.g. $NO^2$) and combination thereof. In one embodiment of the invention, the negatively charged groups are sulfur containing acids. In another embodiment of the invention, the negatively charged groups are sulfopropyl (SP). In another further embodiment of the invention, the negatively charged groups are carboxylic acids. In another embodiment of the invention, the negatively charged groups are carboxymethyl (CM).

The support can have a hydrophobic or a hydrophilic surface that binds a part of the negatively charged groups by hydrophobic/hydrophilic covalent interaction. The hydrophobic/hydrophilic surface of the support may also be a polymer such as plastic or any other polymer wherein hydrophobic/hydrophilic groups have been linked to such as polyethylene, polystyrene or polyvinyl. Alternatively, the negatively charged groups can be covalently bound to the support via a linker bridging between the support and the negatively charged groups. The term "linker" as used above refers to a spacer arm or a leash having a molecular weight from tens to million Daltons that is used as an intermediary connector between the support and the negatively charged groups. E.g. the linker can be a protein, a peptide and/or an amino acid. In case the support binds directly the molecule comprising the negatively charged groups (without a linker), a reactive group within the molecule comprising the negatively charged groups, such as a hydroxyl group, an ester or an amino group or carboxy group may be used to join to a reactive group present on the support in order to create the covalent bond. The support may also have a charged surface or can be modified to carry a charged group that interacts with the negatively charged groups. The support may have other reactive groups that can be chemically activated so as to attach the negatively charged groups, for example, cyanogen bromide activated matrices, epoxy activated matrices and the like. The support may also comprise an inorganic carrier such as silicon oxide material, e.g. silica gel, to which the charged groups can be covalently linked. In another embodiment, the charged groups are attached to a membrane surface or are incorporated into the membrane. The attachment of the charged groups to the membrane can be carried out in the same manner as described above.

The cation exchanger used according to the invention can be in the form of a membrane or in the form of a chromatographic material as defined above.

The support comprising the immobilized negatively charged groups is generally referred to as a cation-exchanger. "Cation exchangers" are named for their ability to attract or bind cations or positively charged particles. Typically, the support system is negatively charged and a molecule will bind under a pH which renders the net charge of the molecule positive. Examples of commercially available cation-exchangers in the form of a membrane are Mustang® S membrane and Mustang® S capsule which comprise a sulfonic functional group.

In the case of using a membrane as the support (e.g. Mustang® S membrane, Mustang® S capsule), the immunoglobulin solution may be contacted with the membrane at a fluid flow rate in the range of 2 to 4.3 Membrane Volume (MV)/min. The term "fluid flow rate" normally refers to the flow of the solution through the support.

The term "isoelectric point" refers to the pH wherein a molecule carries no net charge. Below the isoelectric point, the molecule carries a net positive charge, above it the molecule carries a net negative charge.

The support comprising the negatively charged groups can be a weak (e.g. carboxymethyl (CM)-column) or a strong cation exchanger (e.g. Mustang® S membrane). A weak cation exchanger generally refers to an exchanger which is comprised of a weak acid that gradually loses its charge as the pH decreases, while a strong cation exchanger generally refers to an exchanger which is comprised of a strong acid that is able to sustain its charge over a wide pH range.

The term "contacting" refers to any type of a combining action which brings the solution or fraction into sufficiently close contact with the support and more particularly with the charged groups of the support in a manner that a binding interaction will occur between the charged groups and any binding partner, e.g. a thrombogenic agent, present in the solution/fraction. The solution/fraction can be incubated with the support for a sufficient period of time which allows binding between the charged groups and the thrombogenic agent. The solution/fraction can be in a temperature in the range of 7° C. to 37° C. while contacting the support.

It was found according to the present invention that carrying out a second cation exchanger chromatography step resulted in an increased removal of FXIa from the immunoglobulin containing solution as compared to carrying out a single cation exchanger chromatography step. This second cation exchanger chromatography step was carried out while substantially preserving the IgG levels. Thus, the solution can be contacted with the support several times. Alternatively, when the support is a filter, more than one filter can be combined into a single functional unit. In one embodiment of the invention, the first filtration step results in an unbound fraction I which is contacted with the support comprising the immobilized negatively charged groups under the same pH range specified above, and a second unbound fraction II is collected.

The support can be equilibrated prior to contacting the solution/fraction with a buffer e.g. by washing the support with the buffer of the immunoglobulin containing solution.

The term "equilibrate" generally refers to allowing the column or support to reach a specific buffer condition such as a specific pH level and/or ionic strength.

The term "un-bound fraction" typically refers to the flow through material obtained or collected following contacting the immunoglobulin containing solution with a support comprising charged groups or to the flow through material that is obtained or collected following contacting an immunoglobulin containing solution/fraction with a chromatography support.

In one embodiment, the charged groups are negatively charged. In another embodiment, the flow through material obtained is referred to as "un-bound fraction I". In another embodiment, "un-bound fraction I" is subjected to the support comprising the negatively charged groups, and the flow through material is referred to as "un-bound fraction II".

A chromatographic column can be prepared by packing a dry chromatographic material or a pre-swollen material into a column. Dry chromatographic material can be pre-treated by stirring the material in 2 volumes of 0.5 N HCl (for obtaining a support comprising negatively charged groups) or in 0.5 N NaOH (for obtaining a support comprising positively charged groups). The material can then be allowed to settle e.g. for about 30 minutes. The supernatant can be decanted and the material can be washed with $H_2O$ until a pH value of 4 or 8, respectively, is reached. The material can then be suspended in 2 volumes of 0.5 N NaOH (for a support comprising negatively charged groups) or in 0.5 N HCl (for a support comprising positively charged groups), and the supernatant can be decanted e.g. after 30 min. The second suspension step can be repeated, and the column can then be washed with $H_2O$ until the filtrate is neutral.

A pre-swollen material (and the dry material treated as described in the above paragraph) can be pre-treated by stirring the material for e.g. 5 min with the buffer used for loading the immunoglobulin containing solution in a ratio of 6 ml buffer/gram pre-swollen material (or 30 ml buffer/gram dry material). The pH can then be adjusted to according to the invention, and the material is allowed to settle e.g. for about 30 min, and the supernatant is decanted. The slurry is then re-dispersed in equilibration buffer (ratio as above). For column packing, the material is then allowed to settle.

Alternatively, a commercially available pre-packed ready-to-use-column can be used without any pre-treatment.

Afterwards, the column (prepared from the dry material, pre-swollen material, or the pre-packed ready-to-use-column) is packed, and equilibrated to the desired pH conditions (e.g. by using equilibration buffer).

After column equilibration, the immunoglobulin solution having the desired pH is loaded and the column can be washed with about five bed volumes equilibration buffer to wash out all unbound material. The column can be cleaned for a second use.

Preparation and pre-treatment of the chromatographic material, column packing, column equilibration, loading of the immunoglobulin containing solution, collection of unbound material, and column cleaning for a second use are well known in the art see, for example, Protein liquid chromatography, Edited by Michael Kastner, Elsevier science B.V. 2000, pages 45-49.

The immunoglobulin containing solution can be subjected to a filtration step prior to chromatography in order to reduce aggregates in the solution. The filtration can be carried out e.g. through a 1.2 μm depth filter or 0.2 μm filter. In one embodiment of the invention, prior to carrying out the anion exchange chromatography, the solution is subjected to 0.2 μm positively charged depth filter. Advantageously, the positively charged depth filter is used to remove negatively charge materials such as phospholipids, lipids and the like. An anion exchanger chromatography can be carried out using 7.5 L of resin e.g. diethylaminoethyl (DEAE) resin packed in a column e.g. having a diameter of 35 cm and a bed height of 15 cm. The packed column can be equilibrated with at least 48 column volume of Purified Water (PuW) or Water for Injection (WFI) at a fluid flow rate of 100-120 L/hour e.g. at a fluid flow rate 110 L/hour. After equilibration, 18 column volume of immunoglobulin containing solution can be loaded into the column. Loading of the immunoglobulin containing solution can be carried out at a fluid flow rate of 50-70 L/hour e.g. at a fluid flow rate of 60 L/hour. The solution can be at a temperature of 2-10° C. e.g. at 8-10° C. The chromatography can be carried out at room temperature (22±2° C.).

A cation exchanger chromatography can be carried out using a cation exchange filter membrane having a membrane volume of 1560 ml. Various combinations of membrane sizes can be used to obtain a final membrane volume of 1560 ml e.g. two filter membranes having a volume of 780 ml can be connected in tandem to form a total membrane volume of 1560 ml.

The cation exchanger can be pre-conditioned with at least 38 membrane volume of 1 N NaOH followed by at least 64 membrane volume of 1 N NaCl at a fluid flow rate of 1.6-2.3 L/min. The term "pre-conditioning" generally refers to washing the support or membrane prior to use in order to remove un-wanted substances that may be present on the surface of the support or membrane. Afterwards, the filter membrane can be equilibrated with at least 64 membrane volume of 20 mM Sodium Acetate (adjusted to the desired pH) at a fluid flow rate of 1.6-2.3 L/min until the desired pH is achieved. After equilibration, at least 50-140 membrane volume of immunoglobulin containing solution can be filtered through the filter membrane. The chromatography can be carried out at room temperature (22±2° C.) at a fluid flow rate of 1.6-2.3 L/min. The temperature of the loaded solution can be 6-10° C.

The protein concentration in the immunoglobulin containing solution can be in the range of 40 to 75 mg/ml during loading to the cation or anion exchangers e.g. a protein concentration of 45, 50, 55, 60, 65, 70, 75 mg/ml.

In the case of column chromatography, an un-bound fraction can be obtained following washing of the loaded column with the same buffer used for equilibration and/or the buffer used for loading (oftentimes referred as to "binding buffer") of the immunoglobulin containing solution onto the column.

It was also found according to the present invention that Benzamidine Sepharose (which affinity binds serine proteases such as FXIa) affinity-chromatography was not suitable for removing FXIa from an immunoglobulin containing solution. However, it was surprisingly found that FXIa can be effectively removed from an immunoglobulin solution by subjecting the immunoglobulin solution to heparin—affinity chromatography at a low pH level (e.g. a pH level of 5.3).

Without being bound by the mechanism it appears that at low pH levels heparin—affinity chromatography acts as a cation-exchanger (having acidic groups such as COOH and $H_2SO_4$) and thus can be advantageously used for effectively removing FXIa from an immunoglobulin containing solution in accordance with the invention.

"Affinity chromatography" is generally based on a highly specific biological interaction such as that between antigen and antibody, enzyme and substrate, or receptor and ligand.

In one embodiment of the invention, a FXIa removal of more than 75% e.g. 80%, 85%, 90%, 95% and 99% from the immunoglobulin containing solution or fraction as compared to the initial FXIa content (before contacting the solution or the fraction with the support comprising the immobilized negatively charged groups according to the invention) is considered efficient.

In one embodiment of the invention, a kallikrein removal of more than 75% e.g. 80%, 85%, 90%/a, 95%, 97% and 99% from the immunoglobulin containing solution or fraction as compared to the initial kallikrein content (before contacting the solution or the fraction with the support comprising the immobilized negatively charged groups according to the invention) is considered efficient.

PKA has a zero net electrical charge at pH level in the range of 7-8.2 (the isoelectric point of PKA is about 8; http://www.expasy.org) and as such it is not expected to bind to positively charged groups. Nevertheless, it was found according to the present invention that subjecting an immunoglobulin solution with a pH level in the range of 7-8.2 to an anion-exchanger resulted in effective PKA removal. The results also show that using a pH level range of 7-8.2 in an anion-exchanger chromatography also resulted in high IgG recoveries in the un-bound fraction. A pH of 7-8.2 is a level wherein the IgG has zero or negative net charge and thus, it was expected that some of it would be lost due to binding to the anion exchanger. It was surprisingly found that subjecting an immunoglobulin containing solution to an anion exchanger at a pH level range of 7-8.2 resulted in maximal removal of PKA and, practically, no loss of IgG.

Accordingly, in order to remove PKA and at the same time obtain a high immunoglobulin recovery, the method according to the invention can further comprise a step of contacting the immunoglobulin containing solution/fraction with a support comprising immobilized positively charged groups at a pH in the range of 7 to 8.2, and collecting the unbound fraction. Thus, the immunoglobulin containing solution is subjected to an anion exchanger at a pH in the range of 7 to 8.2.

In one embodiment, the method employs first the anion exchanger step followed by the cation exchanger step of the invention. In another embodiment, the method employs first the cation exchanger step followed by the anion exchanger step.

In one embodiment, the pH of the immunoglobulin containing solution is adjusted with an acid or base solution to a pH in the range of 7 to 8.2 and the solution is contacted with the positively charged groups pre-equilibrated with a buffer or PuW having the same pH as the solution and the unbound fraction is collected. The pH of the collected fraction can be adjusted with an acid solution to a pH in the range of higher than 3.8 and equal to or lower than 5.3 and the fraction can be contacted with the negatively charged groups pre-equilibrated with a buffer having the same pH as the fraction and the unbound fraction is collected.

In another embodiment, the pH of the immunoglobulin containing solution is adjusted with an acid or base solution to a pH in the range of higher than 3.8 and equal or lower than 5.3 and contacted with the negatively charged groups pre-equilibrated with a buffer having the same pH as the solution and the unbound fraction is collected. The pH of the collected fraction can be adjusted with a base solution to a pH in the range of 7 to 8.2 and contacted with the positively charged groups pre-equilibrated with a buffer or PuW having the same pH as the fraction and the unbound fraction is collected.

In one embodiment of the invention, the anion and cation exchanger steps are one immediately after the other. In another embodiment of the invention, there are additional steps in between the anion and cation exchanger steps of the invention.

The steps of anion or cation exchanger can be carried out several times to increase purification.

The term "positively charged groups" as used herein refers to a molecule comprising chemical groups which carry a positive charge such as ammonium, alkyl ammonium, dialkylammonium, trialkyl ammonium, quaternary ammonium [e.g. diethylaminoethyl (DEAE), a dimethylaminoethyl or a trimethylaminoethyl], alkyl groups, $H^+$, $Na^+$, $K^+$, $Ca^{2+}$, $Mg^{2+}$, amino functional group (e.g. $NR_2H^+$), and combination thereof.

In one embodiment of the invention, the positively charged groups are quaternary ammonium (Q). In another embodiment of the invention, the positively charged groups are Diethylaminoethyl (DEAE).

In one embodiment of the invention, the immunoglobulin containing solution is first contacted with the support comprising the immobilized positively charged groups at a pH in the range of 7 to 8.2, the un-bound fraction is collected; then the un-bound fraction is contacted with the support comprising the immobilized negatively charged groups; and an un-bound fraction I is collected. Alternatively, the immunoglobulin containing solution can be first contacted with the support comprising the immobilized negatively charged groups; an "un-bound fraction I" is collected; and then un-bound fraction I is contacted with the support comprising the immobilized positively charged groups and an "un-bound fraction" is collected.

The support comprising the positively charged groups can be composed of any material which is capable of binding a molecule comprising chemical groups which carry a positive charge as defined above.

The support comprising the immobilized positively charged groups is generally referred to as an anion-exchanger. "Anion exchangers" are named for their ability to attract or bind anions or negatively charged particles. Anion exchangers are well known in the art (Practical Protein Chromatography edited by Kenney and Fowell Volume 11 Humana Press, 1992). In anion exchangers, the support system is positively charged and a molecule will bind if the buffer pH is higher than the protein's unique isoelectric point.

The support comprising the immobilized positively charged groups can be a weak or a strong anion exchanger. A weak anion exchanger generally refers to an exchanger which is comprised of a weak acid that gradually loses its charge as the pH decreases, while a strong anion exchanger generally refers to an exchanger which is comprised of a strong acid that is able to sustain its charge over a wide pH range.

The solution/fraction can be in a temperature in the range of 8 to 37° C. while contacting the support.

The immunoglobulin containing solution/fraction can be contacted with the support several times and/or two or more filters combined into a single functional unit can be used.

The support can be equilibrated prior to contacting the solution or fraction with the support e.g. by washing the support with the buffer of the immunoglobulin containing solution/fraction.

More specifically, following contacting the solution with the support comprising the immobilized positively charged groups, the un-bound fraction is collected (the flow through material obtained following contacting the immunoglobulin solution with the support). In the case of column chromatography, the un-bound fraction can be obtained following washing of the loaded column with the same buffer used for equilibration and/or the buffer used for loading of the immunoglobulin containing solution/fraction onto the column.

Alternative immobilizing possibilities between the support and the positively charged groups are elaborated above for immobilizing possibilities between the support and the negatively charged groups.

In the case of using a column as the support comprising the positively charged groups, the immunoglobulin containing solution can be contacted with the column at a linear velocity between 1 and 2 ml/min/cm². The term "filtration linear velocity" refers to the velocity of a solution that flows through a column.

The invention also provides a method for removing a thrombogenic agent from an immunoglobulin containing solution comprising the steps of: providing the immunoglobulin containing solution at a pH in the range of 7 to 8.2, providing a support comprising immobilized positively charged groups, and providing a support comprising immobilized negatively charged groups; contacting the solution with the support comprising the immobilized positively charged groups; collecting the un-bound fraction; adjusting the pH of the fraction to a pH in the range of higher than 3.8 to equal to or lower than 5.3; contacting the un-bound fraction with the support comprising the immobilized negatively charged groups; and collecting an unbound fraction I.

In one embodiment of the invention, detectable amounts of thrombosis-generating agents (e.g. PKA, kallikrein and/or FXIa) are removed from the immunoglobulin containing solution.

The term "detectable" refers, for example, to a level detected using a method of analysis as described below in the Materials and Methods section.

In one embodiment of the invention, a PKA removal of more than 80% e.g. 83%, 85%, 90%, 95% and 99% from the immunoglobulin containing solution or fraction as compared to the initial PKA content (before contacting the solution or the fraction with the support comprising the immobilized positively charged groups according to the invention) is considered efficient. The findings according to the invention also show that using an SDR-column made of a three-dimensional cross-linked hydrophobic acrylic polymer resulted in removal of residual amounts of FXIa. An SDR-column is a chromatographic technique in which the sample interacts, at a relatively high mobile phase salt concentration, with a hydrophobic stationary phase.

Accordingly, the immunoglobulin containing solution can be also contacted with a chromatographic material comprising three-dimensional cross-linked hydrophobic acrylic polymer, and an unbound fraction (e.g. "unbound fraction III") is then collected. Alternatively, the contacting with the chromatographic material comprising the three-dimensional cross-linked hydrophobic acrylic polymer can be carried out after contacting with the support comprising the immobilized negatively charged groups or after contacting with the support comprising the immobilized positively charged groups i.e. "un-bound fraction", "un-bound fraction I", or "un-bound fraction II" are contacted with the chromatographic material comprising the three-dimensional cross-linked hydrophobic acrylic polymer, and an unbound fraction III is then collected. An example of such three-dimensional cross-linked hydrophobic acrylic polymer is the HyperD resin supplied by Biosepra. HyperD chromatography involves a mixed-mode of adsorption of hydrophobic interaction and molecular exclusion [Guerrier L et al. "Specific sorbent to remove solvent-detergent mixtures from virus-inactivated biological fluids". J Chromatogr B Biomed Appl. 1995 Feb. 3; 664(1):119-125].

It was observed (using the Wessler animal Model as described in Wessler et al. Biologic assay of a thrombosis-inducing activity in human serum. J Appl Physiol. 1959; 14:943-946) that an immunoglobulin composition subjected to kallikrein, PKA and/or FXIa removal according to the invention exhibited reduced thrombosis-inducing activity.

In one embodiment, the invention provides a method for purifying an immunoglobulin containing solution from thrombogenic agents comprising: subjecting the solution to at least two steps of negative ion-chromatography: an anion exchanger chromatography at a pH in the range of 7 to 8.2; followed by a cation exchanger chromatography at a pH in the range of higher than 3.8 to equal to or lower than 5.3. The method can further comprise the step of subjecting the solution to negative hydrophobic chromatography using a chromatographic material comprising three-dimensional cross-linked hydrophobic acrylic polymer.

The invention also provides a method for preparing an immunoglobulin composition comprising the steps of: subjecting an immunoglobulin containing solution to at least two steps of negative ion chromatography: an anion exchanger chromatography at a pH in the range of 7 to 8.2; followed by a cation exchanger chromatography at a pH in the range of higher than 3.8 to equal to or lower than 5.3.

The cation exchanger chromatography can be carried out at a pH range of higher than 3.8 to equal to or lower than 5.0, at a pH range of equal to or higher than 4.0 to equal to or lower than 5.0, at a pH range of higher than 3.8 to equal to or lower than 4.7, at a pH range of higher than 3.8 to equal to or lower than 4.3, or at a pH range of equal to or higher than 4.0 to equal to or lower than 4.3.

The methods of the invention can further comprise a negative hydrophobic chromatography using a chromatographic material comprising three-dimensional cross-linked hydrophobic acrylic polymer.

In certain embodiments, the flow through material from the cation exchanger according to the invention is named unbound fraction I; the flow through material from the anion exchanger according to the invention is named unbound fraction; the flow through material from a second step of cation exchanger according to the invention is named unbound fraction II; and the flow through from a chromatographic material comprising three-dimensional cross-linked hydrophobic acrylic polymer according to the invention is named unbound fraction III. Each of these fractions can be loaded in one or more of the chromatographic steps and conditions according to the invention in different order to remove thrombogenic agents and to collect the immunoglobulin containing flow through fraction.

In one embodiment of the invention an immunoglobulin containing solution is loaded into the three-dimensional cross-linked hydrophobic acrylic polymer as described in U.S. Pat. No. 6,468,733. The resulting unbound fraction III is collected, the pH of the unbound fraction III is equilibrated to 7-8.2, and the fraction III is subjected to an anion exchanger under similar pH conditions. The unbound fraction is collected, the pH of the unbound fraction is equilibrated according to the invention before loading to a cation exchanger according to the invention, and the unbound fraction I is collected. This last step can be repeated.

The term "negative chromatography" refers to chosen conditions so that only a relatively small proportion (e.g. less than 25%) or none of a purified protein (i.e. immunoglobulin) binds to the chromatography support and it thus passes through the support in the chromatographic separation. The predominant portion of the protein is thus present in the flow through material.

The term "positive chromatography" refers to chosen conditions so that the majority of a purified protein (i.e. immunoglobulin) binds to the chromatography support and therefore a step of elution under non isocratic conditions is required to recover the protein.

The results show that an efficient removal of thrombogenic agents was obtained also in scale-up process of cation and anion exchanger chromatography.

The invention also provides an immunoglobulin composition comprising low levels of a thrombogenic agent. The immunoglobulin can be provided in a liquid or solid form e.g. as a lyophilized powder.

In one embodiment of the invention, the immunoglobulin containing solution is first contacted with the support comprising the immobilized positively charged groups (anion exchanger); the resulting unbound fraction is collected and contacted with the support comprising the immobilized negatively charged groups (cation exchanger) and the resulting unbound fraction I which comprises immunoglobulin composition with low thrombogenic agents is collected. In one embodiment of the invention, the immunoglobulin containing solution is also contacted with a chromatographic material comprising three-dimensional cross-linked hydrophobic acrylic polymer (hydrophobic chromatography-HIC).

An immunoglobulin composition with low levels of a thrombogenic agent refers, for example, to a composition having less than 6 IU/ml PKA; to a composition exhibiting a thrombin generation of less than about 100 nM when determining the formation of thrombin in the immunoglobulin composition e.g. by carrying out a Thrombin Generation Assay as described below; less than 0.8 ng/ml FXIa; and/or less than 200 ng/ml kallikrein (e.g. less than 126 ng/ml). PKA, kallikrein and FXIa levels can be determined by carrying out an assay as described below in the Materials and Methods section.

In another aspect the invention relates to an immunoglobulin composition obtainable according to the method of the invention. The immunoglobulin composition can be provided in a receptacle. The vial or pre-filled syringe can contain different volumes of the composition, for example, the composition can have a volume of 0.5 ml, 2 ml, 10 ml, 30 ml, 50 ml, 100 ml, 200 ml, 500 ml, 1 liter, 2 liter and 3 liter.

The term "receptacle" refers to any container designed for holding the immunoglobulin composition.

The immunoglobulin composition can comprises a protein concentration in the range of 2 to 20% w/v, or 5-10%/0. In one embodiment of the invention, the composition has a protein concentration in the range of 4.5-5.5% w/v. In another embodiment of the invention, the composition has a protein concentration of about 5% w/v. In another embodiment, the composition has a protein concentration of about 10% w/v. In one embodiment the protein concentration is about 50 mg/ml. The % of immunoglobulin out of total protein content can be above 90%. In one embodiment of the invention, the percentage of immunoglobulin out of total protein content is 95%.

In another embodiment of the invention, the immunoglobulin composition comprises a low percentage of protein aggregates e.g. less than 3% protein aggregates.

The term "aggregates" refers to a chunk of material which contains solids such as protein aggregates. The aggregates can be measured by HPLC.

In one embodiment of the invention, the composition is provided in a volume of 50 ml and has a protein content of 2.5 g. In another embodiment of the invention, the composition is provided in a volume of 100 ml and has a protein content of 5.0 g. In another embodiment of the invention, the composition is provided in a volume of 200 ml and has a protein content of 10.0 g.

Vials comprising the composition can be stored at a temperature of lower than 25° C., such as at a temperature of 0° C. or 2° C. to 8° C. and protected from light until use.

The immunoglobulin composition can also comprise excipients. As used herein the terms "excipient" refers to an inert substance which is added to the pharmaceutical composition. The excipients can be added into the composition, for example, in order to ensure that the active ingredient retains its chemical stability and biological activity upon storage, to aid the manufacturing process and/or for aesthetic reasons e.g. color. Examples of excipients include, but are not limited to, various sugars, such as maltose or, D-sorbitol; glycine; polymeric excipients, such as PEG or serum proteins, such as albumin.

The immunoglobulin composition can comprise at least 95% Human Normal Immunoglobulin G as the active ingredient, 10%/maltose and Water for Injection. The Immunoglobulin A (IgA) content can be equal to or less ≤0.15 mg/ml.

Yet another object of the invention is accomplished by providing a method for treating a subject suffering from an immunodeficiency e.g. primary and secondary immunodeficiency, an inflammatory disease, an autoimmune disease, or an acute infection, comprising administering to the subject an effective amount of an immunoglobulin composition according to the invention.

The term "subject" includes animals of mammalian origin, including humans. In one embodiment, the subject is a patient.

The term "an effective amount" refers to the dose required to prevent or treat (relieve a symptom or all of the symptoms) a disease, disorder or condition. The effective amount can be measured based on any change in the course of the disease in response to the administration of the composition. The effective dose can be changed depending on the age and weight of the subject, the disease and its severity (e.g. early or advanced stage) and other factors which can be recognized by the skilled in the art.

The immunoglobulin composition can be used for replacement therapy such as in primary immunodeficiency (patients with primary defective antibody synthesis such as agammaglobulinemia or hypogammaglobulinemia); Chronic Lymphocytic Leukemia (CLL) with severe secondary hypogammaglobulinemia and recurrent infections, in whom prophylactic antibiotics have failed; Myeloma in plateau phase with hypogammaglobulinemia and recurrent bacterial infections who have failed to respond to pneumococcal immunization; Hypogammaglobulinemia I patients after allogeneic hematopoietic stem cell transplantation (HSCT); Children with congenital AIDS and recurrent infections; and Allogenic Bone Marrow Transplantation; and in Immunomodulation such as in Chronic inflammatory demyelinating polyneuropathy (CIDP); Idiopathic Thrombocytopenic Purpura (ITP); Guillain Barré Syndrome; and Kawasaki Disease.

The dose and dosage regimen is dependent on the intended use. In replacement therapy, the dosage may need to be individualized for each patient, dependent on the pharmacokinetic and clinical response.

The immunoglobulin composition prepared according to the invention which has low levels of thrombogenic agents can be administered by routes that lead to systemic absorption. Non limiting examples of administration routes include, but are not limited to, intravenous, subcutaneous, intraperitoneal, and intramuscular. Advantageously, patients may receive a high dose of the immunoglobulin solution prepared according to the invention which has low levels of thrombogenic agents. The administration can be carried out in an initially higher dose e.g. 0.4-0.8 g/kg followed by the same or lower doses at intervals. The higher doses can be intended to rapidly increase the patient's immunoglobulin concentration to an efficacious target concentration.

The term "intravenous" refers to administration of the composition into the vein of a subject. The administration can be intermittent or by continuous dripping. The term "intermittent" is synonymous with the term "intravenous bolus" or "intravenous push".

The term "subcutaneous" refers to introduction of the composition by injection under the skin of a subject. The injection can be carried out by creating a pocket such as by pinching or drawing the skin up and away from underlying tissue. Optionally, the infusion may be carried out by subcutaneous implantation of a drug delivery pump implanted under the skin of the subject. The pump can deliver a predetermined amount of the immunoglobulin at a predetermined rate for a predetermined period of time.

By "intramuscular" it is meant an introduction of the immunoglobulin composition directly into a muscle. The injections can be given into any muscle including, but not limited to, the deltoid, vastus lateralis, ventrogluteal and dorsogluteal muscles. The administration can be carried out at multiple locations. "Intraperitoneal injection" refers to the injection of the immunoglobulin into the peritoneum.

The immunoglobulin composition of the invention can be prepared from blood or blood fractions donated by healthy donors. The immunoglobulin can be prepared from pooled blood or blood fractions obtained from 1000 donors and more. The immunoglobulin can be prepared from screened donors with high titers of antibodies. An example of such a technique is disclosed in WO-2007/017859 which content is incorporated herein by reference. The term "blood fraction" refers to a fraction of whole blood which comprises immunoglobulins such as plasma or serum. The immunoglobulin composition can be obtained by re-suspending Paste II, from plasma fractionation e.g. according to Cohn fractionation and/or Kistler-Nitschmann (KN) fractionation method.

Immunoglobulin compositions derived from blood components are typically purified from infective particles. The viral inactivation can be carried out by filtration, nanofiltration, solvent/detergent treatment, heat treatment, such as, but not limited to, pasteurization, gamma or UVC (<280 nm) irradiation, or by any other method known in the art.

In one embodiment of the invention, the immunoglobulin composition is purified by the solvent-detergent method using TnDD/Triton-X-100, and by nanofiltration at pH-4.

The term "infective particle" refers to a microscopic particle, such as, but not limited to, a microorganism or a prion, which can infect or propagate in cells of a biological organism. The infective particles can be viral particles.

The inactivation procedure of infective particles can be carried out by adding an inactivating molecule to the composition prior to and/or during the purification procedure. The added molecules and their products can be removed by gravitation, column chromatography or by any other method known in the art. The removal of infective particles can be carried out by nanofiltration or by selective absorption methods such as affinity, ion exchange or hydrophobic chromatography. A multi-step viral inactivation procedure can be carried out. For example, the immunoglobulin containing solution can be subjected to solvent/detergent treatment, heat treatment, selective chromatography and nanofiltration.

The term "viral inactivation" refers both to the situation wherein viruses are maintained in the solution but are rendered non-viable (for example, by dissolving their lipid coat), and/or as to the situation wherein viruses are physically removed from the solution (for example, by size exclusion techniques).

"Solvent detergent (S/D) treatment" typically refers to a process that inactivates envelope-coated viruses by destroying their lipid envelope. The treatment can be carried out by the addition of detergents (such as Triton X-45, Triton X-100 or Tween 80) and solvents [such as tri(n-butyl) phosphate (TnBP), di- or trialkylphosphates]. The solvent-detergent combination used to deactivate lipid coated viruses may be any solvent-detergent combination known in the art such as TnBP and Triton X-100; Tween 80 and Sodium cholate and others. The concentration of the solvent detergents can be those commonly used in the art, for example, >0.1% TnBP and >0.1% Triton X-100. Typically, the conditions under which the solvent-detergent inactivates the viruses consist of 10-100 mg/ml of solvent detergent at a pH level ranging from 5-8, and a temperature ranging from 2-37° C. for 30 min. to 24 hours. However, other solvent detergent combinations and suitable conditions will be apparent to any person versed in the art. The bulk of the solvent-detergent used in the S/D treatment can be removed, for example, by using chromatography columns such as hydrophobic interaction chromatography column (HIC) e.g. C-18 silica packing material and SDR (Solvent-Detergent removal) HyperD; protein adsorption matrices such as ion-exchange matrices; affinity matrices; and/or size—exclusion matrices. The S/D removal can further comprise a step of oil extraction.

"Nanofiltration" typically refers to a process by which lipid-enveloped and non-enveloped viruses are excluded from the solution e.g. by using special nanometer-scale filters such as Planova™ 20N, 35N and 75N; Viresolve/70™, Viresolve/180™. The filters can have a pore size of less than 70 nm, preferably between 15 and 50 nm. However, any membrane having a pore size sufficient to reduce or eliminate viruses from the solution can be employed in nanofiltration. Viruses removed by nanofiltration can be enveloped [e.g. HIV, hepatitis B virus, hepatitis C virus, West Nile Virus, cytomegalovirus (CMV), Epstein-Barr virus (EBV), herpes simplex virus], and non enveloped (e.g. hepatitis A virus, paravirus B19, Polio virus).

Examples of immunoglobulin purification techniques are disclosed in U.S. Pat. No. 6,468,733, EP patent No. 1,161,958 and International PCT Publication WO 99/18130 whose contents are incorporated by reference. For example, a method for the purification of immunoglobulins from a source solution such as Cohn Fraction II may comprise: (a) pre-treating a cation exchange resin with an acidic solution having a pH of 4.0-4.5; (b) contacting the source solution with the cation exchange resin; and (c) eluting the immunoglobulins bound to the cation exchange resin. Prior to contact with the cation exchange resin, the source solution may be treated with an organic solvent and detergent.

Another method for the purification of immunoglobulins may comprise: (a) treating the solution with a solvent-detergent combination, at concentrations and under conditions which are sufficient to inactivate lipid-coated viruses; (b) removing the solvent-detergent combination from the solution by passing the solution obtained in (a) on a chromatographic packing composed of silica beads which pore volume is filled with three-dimensional cross-linked hydrophobic acrylic polymer, and (c) passing the solution of step (b) through a filter having a pore size from about 15 nm to about 70 nm as described in U.S. Pat. No. 6,468,733.

The immunoglobulin composition can be concentrated by ultra-filtration process. The ultrafiltration can be followed by diafiltration to exchange the buffer. The concentration and dialysis by ultrafiltration and diafiltration, respectively, can be performed in one step or as two separate steps. The diafiltration can be carried out against any solution which is suitable for human administration. Non limiting examples of such solutions include, but are not limited to, 0.3% NaCl and from about 1.6 to about 2.6% glycine such as about 2.25%.

EXAMPLES

Materials and Methods
Immunoglobulin Solution.

a) Paste II Resuspension.

Paste II (45 Kg), prepared from plasma by the Cohn fractionation method (Cohn, E. J. The history of plasma fractionation. In Advances in Military Medicine, Andrus et al. Eds. Little, Brown & Co, 1948), was transferred to a crusher tank to which cold (4° C.) Water for Injection (WFI) (3 times the weight of paste II) were added to achieve a final weight of 180 Kg. The re-suspended paste was first stirred for a period of about 5 hours at 4-6° C., and then decanted at 4-6° C. without stirring for about 37 hours, to allow precipitation of major protein aggregates. Following precipitation the supernatant was separated from the precipitate and was used for the following step.

b) CUNO Filtration

The supernatant obtained in the previous step was filtered through a parallel pair of CUNO 0.2 μm positively charged depth filters (Cuno Zeta Plus, Cuno incorporation Inc. CT USA), in order to remove aggregates. The filter pressure did not exceed 1.0 Bar during the filtration step. The fluid flow rate during the filtration was 60 L/h and the temperature was 7.2° C.

c) Anion-Exchange Chromatography—Diethylaminoethyl Cellulose (DEAE)—Column.

In the next step, the solution resulting from step b) was subjected to an anion exchanger (see Examples 7-11).

Unless otherwise indicated, the DEAE-column was equilibrated with 7 column value (CV; i.e. 77 ml) of Pure Water (or WFI) at a fluid flow rate of 2.8 ml/min. After equilibration, the immunoglobulin solution resulting from step b) was loaded into the column. The column pressure did not exceed 1.0 Bar.

In the case of further processing, step c) unless otherwise indicated, was carried out using the following conditions (scale-up conditions): DEAE-column (Toyopearl DEAE-650M; TOSOHAAS) was used as the anion exchanger [7.5 L resin. The column's diameter was 35 cm; and a bed height of 15 cm]. The column was washed with 360 L of WFI at a fluid flow rate of 110 L/hour. The loading was carried out as a continuation to the CUNO filtration at a fluid flow rate of 60 L/hour at 8-10° C. (material temperature). The loading volume of the immunoglobulin solution was 18 column volumes, the pH of the subjected solution was 7-7.6. The Chromatography was carried out at room temperature (22±+2° C.).

d) pH Adjustment

The pH of the solution was adjusted to 4.59 by adding 0.5 M HCl under continuous agitation. The temperature was maintained at 8±2° C. In order to remove aggregates, the solution was filtered through 0.45 μm-0.65 μm filter (Sartobran) into a clean vessel.

e) Concentration to 90 g/L and Diafiltration

The resulting solution of d) was ultra filtered by using an ultra-filtration cassette containing a membrane with an exclusion limit of 30,000 D (Filtron Maxisette; 30 KD). The cassette was prepared by washing with 500 Kg WFI. During the ultrafiltration, the protein solution (200 Kg) was concentrated to 90 g/L (a final weight of 141 Kg). This step was followed by diafiltration against 705 Kg WFI at constant volume in order to remove the residual ethanol and to decrease the osmolality to <30 mOsm/Kg. The protein concentration was then adjusted to 73 g/L with WFI to reach a final volume of 173 Kg. The temperature was maintained at 8±2° C. throughout this step.

Cation-exchange chromatography [by using Mustang® S membrane, Mustang® S capsule, SP-column or CM-column (for the specific conditions see Examples 2-4, Example 5, Example 1, and Example 1, respectively)] was carried out following step c)—using SP-column or following step e)—using Mustang® S membrane or Mustang® S capsule.

When the cation-exchange chromatography was carried out following step c)—about 50-60 mg/ml protein were subjected to the chromatography. When the cation-exchange chromatography was carried out following step e)—about 70 mg/ml protein were subjected to the chromatography.

In order to reduce aggregates, prior to subjecting the immunoglobulin solution to the cation-exchanger the solution was filtered through a filter [1.2 μm depth filter obtained from Sartorius sartopure (prior to SP-column) or 0.2 μm CA filter obtained from Corning (prior to Mustang® S membrane or Mustang® capsule)].

For SP-column, the column was equilibrated prior to loading the immunoglobulin solution with 20 ml of 20 mM Acetate buffer having a compatible pH level as the immunoglobulin solution to be loaded.

For Mustang® S membrane, the filter membrane was equilibrated prior to loading the immunoglobulin solution with 20 ml of 20 mM Acetate buffer having a compatible pH level as the immunoglobulin solution to be loaded.

For Mustang® S capsule, the capsule was pre-conditioned before equilibration according to the manufacturer's instructions. Unless otherwise indicated, in the next step, the capsule was equilibrated with 600 ml of 20 mM Acetate buffer having a pH level of 4.2.

Solvent/Detergent (S/D) Treatment.

The immunoglobulin solution was equilibrated to pH of 5.3 and subjected to S/D treatment (to inactivate lipid-enveloped viruses) as follows: 1% Triton X-100 and 0.3% tri(n-butyl) phosphate (TnBP) (v/v) were mixed together and then added slowly into the solution while rapidly stirring (20 Hz) the solution. The solution was then incubated for about 4.5 hours at 6.9° C., under constant, gentle stirring. At the end of the incubation period, the temperature was raised to 23° C. over a period of 1-1.5 hours and under agitation (at a speed of 20 Hz). In the next step, the SD-treated solution was sequentially filtered through a 3μ depth filter (Sartorius) followed by a 0.45-0.65 μm membrane filter (Sartorius) (in order to remove gross particulate debris prior to a subsequent step of S/D removal).

S/D Removal by SDR-Column.

Removal of the S/D was carried out by a dedicated column of HyperD solvent-detergent removal chromatography resin (SDR-HyperD by Biosepra). Prior to loading the SD-treated immunoglobulin solution, the column was prepared with 450 Kg of WFI (at a maximal pressure of 0.8 bar) and at a flow rate of 80 L/h. The column length was 54 cm, with a diameter of 28 cm and the resin's volume was 30-32 L. The flow rate was 78 L/h, and 37 Kg of WFI was used to wash the column after loading of the sample to achieve baseline. The total flow through volume collected was 176.7 Kg.

Measurements of Prekallikrein Activator Levels.

Prekallikrein Activator (PKA), the first zymogen in the intrinsic coagulation cascade, activates Prekallikrein to Kallikrein. In this assay, the Prekallikrein (which is added to the tested sample) is activated to Kallikrein by PKA found in the tested sample. The formed Kallikrein then cleaves a Chromogenic substrate (H-D-But-CHA-Arg-pNA) to colored p-nitroaniline (pNA) at a constant rate (see the reaction below). The reaction can be measured spectrophotometrically at 405 nm.

The obtained color is proportional to the amount of PKA present in the tested sample.

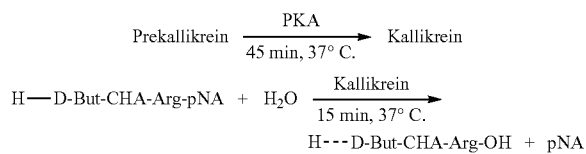

All the required reagents are from the Prekallikrein Activator Assay Kit (Pathway Diagnostics; Product Code: PW30100). The assay was carried out at 37° C.

More specifically, the assay was carried out as follows:

i) Step A for blank preparations: 25 µl of each PKA standard dilutions (0, 3.125, 6.25, 12.5, and 18.75 IU/ml. The various PKA concentrations were prepared from a PKA solution diluted with the buffer's kit); positive control [an FDA International Standard for PKA which contained 10 IU/ml PKA]; or diluted test samples (1:2 dilution with the buffer's kit) were pipetted into a 96-well microplate.

ii) Steps for PKA standards, positive control and test samples: 25 µl of each PKA standard dilution or diluted test samples (the same dilutions as prepared above) were pipetted into an eppendorf tube. Then, 50 µl of Human Prekallikrein solution was added into each eppendorf tube. The tube was capped and mixed and 25 µl from each eppendorf tube was transferred (in duplicates) into microplate wells.

iii) In the next step, the plate was incubated for 30 minutes at 37° C.

iv) Step B for blank preparations: After 30 minutes incubation, 50 µl of a pre-heated (37° C.) Human Prekallikrein solution was added into all blanks (see preparations of step i), and the content of the well was mixed using a pipette. Then, 25 µl of the content of each of these wells was immediately transferred (in duplicates) into corresponding microplate wells. The microplate was incubated at 37° C. for additional about 15 min (a total of 45 min incubation period).

v) Steps for all preparations: 100 µl of pre-warmed (at 37° C.) Kallikrein substrate working solution (a solution comprising the Chromogenic substrate) were added to all the wells (wells of steps ii and iv).

vi) The microplate was placed in an ELISA-reader (at 37° C.) and the optical density (OD) was measured at 405 nm after 2 min ($OD_{2\ min}$) and once more after 12-17 minutes incubation ($OD_{X\ min}$).

The OD obtained for the blanks were subtracted from the OD obtained for the correspondent test samples.

The PKA content was calculated using $\Delta OD_{(x-2)}$ (following subtraction of the blank from each reading) as interpolated from a standard calibration curve taking into account the relevant dilution factor. The results are presented in International Units/ml.

Thrombin Generation Assay—for FXI/FXIa Removal Estimation.

Thrombin Generation Assay (TGA) is a global haemostatic method measuring the amount of thrombin generated and degraded over time. This assay estimates the capacity (or potential) of any given sample to generate thrombin when the coagulation cascade is triggered (either by an intrinsic or an extrinsic trigger). TG is monitored via the conversion of a fluorogenic thrombin substrate and calibration of the thrombin generation of the sample against a defined thrombin activity standard.

The assay was carried out in transparent round bottom (U-bottom) 96-well plates and Thermo Electron Fluorometer ("Fluoroskan FL") equipped with a 390/460 nanometer filter set and a dispenser.

In order to measure FXI/FXIa levels, FXI deficient plasma (obtained from Stago; Catalog Number 00723) was used and the coagulation cascade was triggered by 1 pM Tissue Factor (leads to activation of the extrinsic coagulation pathway) and 4 µM phospholipids (leads to activation of the intrinsic coagulation pathway) (Tissue Factor and phospholipids are mixed together and provided in one reagent—PPP-Reagent low; Stago; Catalog Number TS 31.00).

The measurement was carried out according to: "The Thrombogram Guide" (Thrombinoscope BV): outline of the method to measure thrombin generation using the Calibrated Automated Thrombogram" with the following modifications:

For the measurement, 20 µl of the tested sample (serving as a potential source of FXIa) was mixed with 60 µl FXI deficient plasma, and 20 µl PPP-Reagent low in the well.

Each individual sample tested requires a corresponding calibrator sample (which comprises a known amount of thrombin) and the tested sample. For the thrombin calibrator sample measurement, 20 µl of the tested sample, 60 µl FXI deficient plasma, and 20 µl thrombin calibrator (Stago; Catalog Number TS 20.00) were mixed.

The thrombin generation reaction (at 37° C.) was initiated upon addition of 20 µl containing the fluorescent substrate and $Ca^2$ [the fluorescent substrate and $Ca^2$ are provided in Fluca-kit (Stago; Catalog Number TS 50.00) and are mixed together according to the manufacturer's instructions]. The addition of the fluorescent substrate and the $Ca^{2+}$ is carried out automatically by the "Fluoroskan FL".

The amount of generated Thrombin (in nM) was then calculated using the instrument software Thrombinoscope BV (provided with the "Fluoroskan FL"). The final thrombin amount in the tested sample was calculated by reducing the background value from both the tested sample's value and the thrombin calibrator's value and extrapolating the thrombin amount in the sample from the thrombin calibrator value. The background value is obtained with 60 µl FXI deficient plasma supplemented with 20 µl buffer containing 20 mM Acetate buffer.

Measurements of Factor XIa (FXIa) Levels (Fluorogenic Method).

Factor XIa levels were measured by a fluorogenic method. In the method, FXIa cleaves a specific fluorogenic substrate in the presence of calcium. In the cleavage reaction the substrate (which is composed from a fluorescent reporter group 6-amino-1-naphthalene-sulfonamide (ANSN) attached to a tri-peptide sequence) is hydrolyzed between the tri-peptide sequence and the ANSN group. Once cleaved from the peptide moiety, the ANSN group exhibits about a 1000-fold increase in relative fluorescence. This activity is directly related to the amount of Factor XIa in the sample. The developed fluorescence is measured by using an ELISA reader with the following wavelengths: excitation at 350 nm and emission at 470 nm. More specifically, the measurement was carried out as follows:

First stage (1$^{st}$ 96-well plate preparation)—Tested samples were tested either undiluted (in the case the sample is tested after subjecting the immunoglobulin solution to the cation exchanger or diluted (1:10 in the case the sample is tested before subjecting the immunoglobulin solution to the cation exchanger). The dilution was carried out in buffer B [40 mM Hepes, 300 mM NaCl, 4 mM CaCl$_2$, 0.2% polyethylene glycol (PEG) 20 K solution]. 50 µl from the above mentioned samples were added into a well of a 96 well-plate (Costar; Catalog Number 3797) in quadruplicate.

A standard curve was prepared using FXIa (Hematological Technologies Inc.; Catalog Number HCXIA—0160) diluted in buffer A [20 mM Hepes; 150 mM NaCl solution; 0.1% (w/v) BSA] to the following concentrations: 140, 100, 70, 50, and 25 ng/ml. 50 µl of each concentration was added into the wells in quadruplicate. Positive control (an immunoglobulin preparation which contained about 120 ng/ml of FXIa) and blank samples (Buffer A) were added to each plate in quadruplicate (50 µl of each positive and blank samples).

Second stage (2$^{nd}$ 96-well plate preparation)—For the kinetic reaction a second 96-well plate was prepared (Costar; Catalog Number 3695) by the addition of 25 µl FXIa substrate solution (Hematological Technologies Inc., Catalog Number SN-13a) diluted 1:100 in buffer B) into each well of the 96-well plate. Next, 25 µl of all samples prepared in the 1$^{st}$ 96-well plate (tested samples, samples for standard curve preparation, positive control and blanks samples) were transferred into the parallel wells in the second plate and the second plate was transferred immediately into an ELISA reader (SpectraMax). The following parameters were used for the reading: Recording for 15 minutes every 30 seconds; Excitation: 350 nm; Emission: 470 nm; Cutoff: 455 nm; Temperature: 37° C.; The shaker was activated 15 seconds before the first read; and V, rate [Relative Fluorescence Unit (FRU)/min] was measured from 0-900 seconds.

The $V_{max}$ of the kinetic reaction is a calculation of the reaction, using a linear curve fit. A creeping iteration is performed using the $V_{max}$ points and the slope of the steepest line segment is reported as $V_{max}$ rate as the RFU (Relative Fluorescence Unit).

FXIa concentration (ng/ml) in the tested sample was extrapolated by the software from a standard curve generated using FXIa (described above) taking into consideration sample dilution (the blank was subtracted automatically).

Protein content was measured by the Biuret method using the Total protein reagent (Sigma Diagnostic INC., Catalog Number 541-2) according to the manufacturer's instructions.

IgG subclasses distribution was measured using BIND A RID kit for human IgG subclasses Combi kit (The Binding Site Ltd.; Catalog Number RK021) according to the manufacturer's instructions.

Anti-Diphtheria Antibodies titer was measured by Diphtheria kit (VITROTECH) according to the manufacturer's instructions.

Hepatitis B Surface Antigen (anti-HBsAg) Antibody was measured by a kit obtained from Abbott Laboratories; Catalog Number: LBXHBS.

Measurements of Kallikrein Levels (Chromogenic Method).

Kallikrein levels were measured by a chromogenic method. In the method, kallikrein cleaves a specific chromogenic substrate. In the cleavage reaction the kallikrein substrate (which is composed from a chromogenic reporter group para-nitroaniline (pNa) attached to a Kallikrein substrate oligopeptide sequence) is hydrolyzed between the oligopeptide sequence and the pNa group. Once cleaved from the peptide moiety, p-Na exhibits a high absorbance at 405 nm. This activity is directly related to the amount of kallikrein in the sample. The observed absorbance is measured by using an ELISA reader at 405 nm. More specifically, the measurement is carried out as follows:

First stage (1$^{st}$ 96-well plate preparation)—Tested samples were tested either diluted 1:5 (in the case the sample is tested after subjecting the immunoglobulin solution to the cation exchanger or diluted 1:30 (in the case the sample is tested before subjecting the immunoglobulin solution to the cation exchanger). The dilution was carried out in buffer A [20 mM Hepes, 150 mM NaCl, 0.1% w/v BSA]. 50 µl from the above mentioned samples were added into a well of a 96 well-plate (Costar; Catalog Number 3797) in quadruplicate.

A standard curve was prepared using kallikrein (Enzyme Research Laboratories; Catalog Number HPKa-1303) diluted in buffer A to the following concentrations: 400, 200, 100, 50, 25 and 12.5 ng/ml. 50 µl of each concentration was added into the wells in quadruplicate. Two positive controls (immunoglobulin preparations which contained about 70 and 15 ng/ml of kallikrein) and blank samples (Buffer A) were added to each plate in quadruplicate (50 µl of each positive and blank samples).

Second stage (2$^{nd}$ 96-well plate preparation)—For the kinetic reaction a second 96-well plate was prepared (Costar; Catalog Number 3695) by the addition of 25 µl kallikrein substrate solution {Biophen SC31(02) (HYPHEN BioMed, Catalog Number 229031—reconstituted in 5 ml of purified water and then diluted 1:7 in buffer A} into each well of the 96-well plate. Next, 25 µl of all samples prepared in the 1$^{st}$ 96-well plate (tested samples, samples for standard curve preparation, positive control and blanks samples) were transferred into the parallel wells in the second plate and the second plate was transferred immediately into an ELISA reader (SpectraMax). The following parameters were used for the reading: Recording for 15 minutes every 34 seconds; Absorbance: 405 nm; Temperature: 37° C.; The shaker was activated 15 seconds before the first read; and $V_{max}$ rate [OD/min] was measured from 0-900 seconds.

The $V_{max}$ of the kinetic reaction is a calculation of the reaction, using a linear curve fit. A creeping iteration is performed using the $V_{max}$ points and the slope of the steepest line segment is reported as $V_{max}$ rate as the Absorbance Units/min.

Kallikrein concentration (ng/ml) in the tested sample was extrapolated by the software from a standard curve generated using Kallikrein (described above) taking into consideration sample dilution (the blank was subtracted automatically).

Example 1

The Effect of pH Level of an Immunoglobulin Solution on Efficacy of Cation Exchange Chromatography to Remove FXIa from the Solution The following experiment was aimed to determine the effect of the pH level of the immunoglobulin solution on FXIa removal from the solution by a cation-exchanger.

The isoelectric point of FXIa is about 9 (Bonno B N, Griffin J H. Human blood coagulation factor XI: purification, properties, and mechanism of activation by activated factor XII. J Biol Chem 1977; 252:6432-6437). Since a cation exchanger is used, a pH level of lower than the isoelectric point (wherein FXIa has a net positive charge) can be used. In this experiment, the effect of a pH level range of 4-7 was evaluated.

For this purpose, an immunoglobulin solution was prepared according to steps a-c described in the Material and Methods section. In the next step, the pH of the solution was adjusted either with 0.5 N NaCl or with 0.1 N NaOH to the desired tested pH (a pH range of 4-7; the pH level of the solution was measured using an electronic pH monitoring device.) and 100 ml of each of the resulting immunoglobulin solutions was subjected to the cation-exchanger column.

Sulfopropyl-column (SP-column) was used as the cation-exchanger. Column's preparation: 4 ml of SP resin (TOSOHAAS; Catalog Number Toyopearl, SP-650M) were mounted inside a 1 cm diameter column (Bio-Rad) achieving a bed height of 6 cm. The chromatography was carried out at room temperature (22±2° C.) at a flow rate of 2 ml/min. The temperature of the loaded solution was 22±2° C.

To evaluate the removal of FXIa, the level of FXIa was measured in the loading material ("Load") and after collecting the solution from the column ("Un-bound"). The measurement was carried out by the TG assay as described in the Materials and Methods section. In this experiment, thrombin generation values in the loading material were in the range of 246-271 nM.

To estimate the IgG recovery in the un-bound fraction, the total protein recovery (%) was measured (the IgG consists of about 95% of the total protein). The results are presented in Table 1 below.

The isoelectric point of IgG is 6-8. Thus, at a pH level of lower than 6 the IgG (which has a positive net charge) may be bind to the cation exchanger as well (in addition to the FXIa) thereby resulting in low IgG recoveries.

TABLE 1

The effect of pH level of an immunoglobulin solution on the efficacy of a cation-exchanger to remove FXIa from the solution and on the total protein recovery.

| pH level of the loading material | Sample | Thrombin (nM) | Total protein recovery (%)* |
|---|---|---|---|
| 4 | Un-bound | 40.5 | 97.2 |
| 4.6 | Un-bound | 42 | 92.6 |
| 5.3 | Un-bound | 48.7 | 91.1 |
| 5.7 | Un-bound | 68.9 | 92.1 |
| 6.1 | Un-bound | 71 | 92.8 |
| 6.5 | Un-bound | 102.6 | 98.1 |
| 7 | Un-bound | 110.8 | 94 |

*The evaluation was carried out by comparing the protein content (using the Biuret method) before ("load") and after ("un-bound") subjecting the solution to the column.

The results show that pH levels of higher than 6 resulted in poor FXIa removal (high TG values) and pH levels of lower than about 6 resulted in a high removal of FXIa (low TG values) from the immunoglobulin solution and at the same time with a high IgG recovery (as measured by the total protein recovery). These results are surprising since at pH level lower than 6, the IgG (having an isoelectric point of 6-8) has a positive net electrical charge and as such was expected to bind to the negatively charged groups of the cation-exchanger column and thus low IgG recovery were expected.

Another set of experiments were carried out using a carboxymethyl (CM)-column (a weak cationic exchanger obtained from TOSOHAAS; Catalog Number Toyopearl, CM-650M). The experiment was carried out in the same conditions as the SP-column. With the CM-column only a low pH range of 4-5.5 was examined. The results were comparable with the results obtained with the SP-column showing that at the tested pH (4-5.5) a high removal of FXIa and at the same time a high IgG recovery was obtained. The resin's volume was 8 ml; the column's diameter was 1 cm and the bed height was 10 cm.

Example 2

The Effect of pH Level of an Immunoglobulin Solution on Efficacy of Mustang® S Membrane (a Cation-Exchanger) to Remove FXIa from the Solution The following experiment was aimed to examine the effect of low pH levels of the IVIG solution on FXIa removal from the solution by using Mustang® S membrane cation-exchanger [coin filters; Membrane Bed Volume (MV)=0.35 ml; Pall; Catalog Number NP8MSTGSP1)]. In this experiment the effect of a pH level range of 3.8-5.3 of the immunoglobulin solution on FXIa removal was evaluated.

For this purpose, an immunoglobulin solution was prepared according to steps (a) through (e) described above in the Materials and Methods section. In the next step, the pH of the diafiltrated solution was adjusted with 0.5 N NaCl or 0.1 N NaOH to the desired tested pH (a pH range of 3.8-5.3) and 30 ml of each of the resulting immunoglobulin solutions was subjected to the Mustang® S membrane. The chromatography was carried out at room temperature (22±2° C.) at a flow rate of 1.5 ml/min. The temperature of the loaded solution was 22±2° C.

The level of FXIa was measured in the immunoglobulin solution before ("Load") and after ("Un bound") subjecting the solutions to the cation-exchanger. The evaluation was carried out by a fluorogenic method as described in the Materials and Methods section under "Measurements of FXIa levels". The results are presented in Table 2 below.

TABLE 2

The effect of pH level of an immunoglobulin solution on the efficacy of a cation-exchanger to remove FXIa.

| pH level of the loading material | FXIa (ng/ml) Using a fluorogenic method | | FXIa removal (%)* |
|---|---|---|---|
| | Load | Un-bound | |
| 3.8 | 270.5 | 129.2 | 52.24 |
| 4 | 302.2 | 34.5 | 88.58 |
| 4.3 | 422.4 | 50.1 | 88.09 |
| 4.5 | 360.2 | 67.8 | 81.18 |
| 4.7 | 312.7 | 53.9 | 82.76 |
| 5 | 367.8 | 76.6 | 79.17 |
| 5.3 | 340.9 | 81.4 | 76.12 |

*Calculated by comparing the FXIa levels before ("load") and after ("un-bound") subjecting the solution to the column.

The results obtained show that pH levels higher than 3.8 resulted in efficient removal of FXIa from the immunoglobulin solution with the optimal pH level being at a range of 4.0 to 5.0 (pH in which the highest percentage of FXIa removal was observed).

In another set of experiments the effect of a higher pH level was evaluated (up to 7.4). The experiment was carried out in the same manner as the previous experiment except that 20 ml immunoglobulin solutions was loaded to the cation-exchanger (Mustang® S membrane); and the filtration was carried out at a higher flow rate of 2.5 ml/min.

The level of FXIa was measured in the loading material ("Load") and in un-bound fraction 10 (10 fractions of 2 ml were collected and the measurement was carried out on fraction 10). The measurement was carried out as above by the fluorogenic method. The results are presented in Table 3 below.

TABLE 3

The effect of pH level of an immunoglobulin solution on the efficacy of Mustang ® S membrane to remove FXIa.

| pH level of the loading material | FXIa (ng/ml) Using a fluorogenic method | | FXIa removal (%)* |
| --- | --- | --- | --- |
| | Load | Un-bound fraction 10 | |
| 5 | 116.7 | 28.3 | 75.75 |
| 6 | 115.6 | 68.5 | 40.74 |
| 7.4 | 112.1 | 144.5 | — |

*Calculated by comparing the FXIa levels before ("load") and after ("un-bound") subjecting the solution to the column.

Surprisingly, the results obtained show that although FXIa has a positive net charge in a pH level of lower than about 9 (its isoelectric point is 8.9-9.1), inefficient FXIa removal was obtained at pH of 6 and higher.

Example 3

The Effect of Fluid Flow Rate on the Removal of FXIa from an Immunoglobulin Solution by Cation-exchange Chromatography The following experiment examines the effect of fluid flow rate on the removal of FXIa from an immunoglobulin solution by a cation-exchange chromatography. The following flow rates were evaluated: 0.7, 1, 1.5, 2.5 ml/min. The starting immunoglobulin solution used was as in Example 2 and the same Mustang® S membrane was used as the cation-exchanger. In view of the previous Examples, the pH of the immunoglobulin solution was adjusted to 4.2 (for an immunoglobulin solution loaded at a flow rate of 0.7, 1 and 2.5 ml/min) or 4.3 (for an immunoglobulin solution loaded at a flow rate of 1.5 ml/min) prior to loading the immunoglobulin solution to the cation-exchanger. The chromatography was carried out at room temperature (22±2° C.), the temperature of the solution loaded on the cation exchanger was 22±2° C. and a volume of 30 ml immunoglobulin solution was applied to the cation-exchanger.

The level of FXIa was measured in the immunoglobulin solution before ("Load") and after ("Un bound") loading the solutions to the cation-exchanger. The measurement was carried out directly by the fluorogenic method and indirectly by the TG assay as described bove in the Material and Method section. In this experiment, thrombin generation values in the loading material were in the range of 179-290 nM. The results are presented in Table 4 below.

TABLE 4

The effect of fluid flow rate during cation-exchange chromatography on the removal of FXIa from an immunoglobulin solution.

| Flow rate of the loading material (ml/min) | FXIa (ng/ml) Using a fluorogenic method | | FXIa removal (%)*** | Thrombin (nM) Using the TG assay |
| --- | --- | --- | --- | --- |
| | Load | Un-bound* | | Un-bound* |
| 0.7 | 342.6 | 40.8 | 88.09 | 43.0 |
| 1.0 | 283.5 | 45.1 | 84.09 | 25.2 |
| 1.5 | 422.4 | 50.1 | 88.14 | 0.0 |
| 2.5 | 304.0 | 80.7 | 73.45 | 63.3 |

*For a flow rate of 0.7, 1, and 2.5 ml/min- 15 fractions were collected (each contained 2 ml) and for the evaluation of FXIa levels a mixture of unbound fractions: 2, 5, 7, 10 and 13 was used.
For a flow rate of 1.5 ml/min- the entire un-bound fraction was used for the evaluation.
** Since the Mustang's Membrane Bed Volume (MV) is 0.35 ml- 0.7 ml/min = 2 MV/min; 1 ml/min = 2.9 MV/min; 1.5 ml/min = 4.3 MV/min; and 2.5 ml/min = 7.1 MV/min.
***Calculated by comparing the FXIa levels before ("load") and after ("un-bound") subjecting the solution to the column.

It was observed, according to the fluorogenic method, that the optimal flow rate for removal FXIa from an immunoglobulin solution was in the range of 0.7-1.5 ml/min (the highest FXIa removal percentage was observed in this flow rate range). It is also observed that according to the TG assay, the optimal flow rate for FXIa removal from an immunoglobulin solution (the lowest thrombin level obtained in the un-bound fraction as compared to the other tested flow rates) was 1.5 ml/min.

These results indicate that in order to further improve FXIa removal from an immunoglobulin solution a flow rate of lower than 2.5 ml/min such as a flow rate in the range of 0.7 to 1.5 ml/min (2-4.3 MV/min) can be used during subjection of the solution to the cation-exchanger membrane.

Example 4

The Effect of Temperature Level of an Immunoglobulin Solution on Efficacy of FXIa Removal by Cation-exchange Chromatography The following experiment examines the effect of temperature level of an immunoglobulin solution on FXIa removal by cation-exchange chromatography. For this purpose the immunoglobulin solution was equilibrated to the following temperatures: 7° C., room temperature (22±2), and 37° C. The starting immunoglobulin solution used was as in Example 2 and the same Mustang® S membrane was used as the cation-exchanger.

According to the results obtained in Examples 2 and 3, the pH of the immunoglobulin solution was adjusted to 4.2 prior to subjecting the solution to the cation-exchanger, and the immunoglobulin solution was loaded to the cation-exchanger at a flow rate of 1-1.5 ml/min. The chromatography itself was carried out at room temperature (22±2° C.), and a volume of 30 ml immunoglobulin solution equilibrated to the different temperatures was applied to the cation-exchanger.

The level of FXIa was measured in the immunoglobulin solution before ("Load") and after ("Un-bound") subjecting the solutions to the cation-exchanger. As in Example 3, the evaluation was carried out by the fluorogenic method and the TG assay as described in the Material and Method section. The results are presented in Table 5 below. In this experiment, thrombin generation values in the loading material were in the range of 251-292 nM.

TABLE 5

The effect of temperature level of an immunoglobulin solution on the efficacy of a cation-exchanger to remove FXIa.

| Temperature level of the loading material | FXIa (ng/ml) Using a fluorogenic method | | FXIa removal | Thrombin (nM) Using the TG assay |
|---|---|---|---|---|
| (° C.) | Load | Un-bound | (%)* | Un-bound |
| 7 | 283.9 | 39.0 | 86.26 | 24.9 |
| 22 ± 2 | 283.5 | 45.1 | 84.09 | 25.2 |
| 37 | 274.2 | 49.2 | 82.05 | 59.7 |

*Calculated by comparing the FXIa levels before ("load") and after ("un-bound") subjecting the solution to the column.

The results obtained show that all tested temperature levels resulted in removal of FXIa from the immunoglobulin solution (as compared to the loading material) with the optimal temperature being from room temperature (22±2° C.) down to 7° C.

Example 5

The Effect of Carrying Out a Second Cation-exchange Chromatography Step on the Removal of FXIa from an Immunoglobulin Solution The following experiment examines whether carrying out a second cation-exchange chromatography step would further increase FXIa removal from an immunoglobulin solution.

The starting immunoglobulin solution used was as in Example 2. In the following experiment a volume of 2600 ml of the solution was subjected to Mustang® S capsule having an MV of 10 ml (Pall; Catalog Number CLM05MSTGSP1); the pH of the loaded solution was adjusted to 4.2; and the filtration was carried out at room temperature (22±2° C.) at a flow rate of 30 ml/min (=3 MV/min). The temperature of the loaded solution was 22±2° C.

Six filtrate fractions (400 ml per fraction) were collected and FXIa level was measured using the TG assay as described in the Material and Method section. In the next step, all six filtrate fractions were collected, pooled and subjected to a second filtration step through a new Mustang® S capsule (MV=10 ml). Again, six filtrate fractions (400 ml per fraction) were collected and FXIa level was measured using the TG assay. The results of the loading material and each filtrate fraction (1-6) in each filtration step are summarized in Table 6 below. Also, in order to estimate the IgG recovery, the total protein recovery was measured following the second cation-exchange chromatography step.

TABLE 6

The effect of carrying out a second cation-exchange chromatography step on the removal of FXIa from an immunoglobulin solution.

| Sample | Thrombin (nM) Using the TG assay |
|---|---|
| First Capsule Filtration | |
| Loading material | 248.6 |
| Un-bound (UB) fraction 1 | 0.0 |
| UB fraction 2 | 15.2 |
| UB fraction 3 | 40.0 |
| UB fraction 4 | 62.5 |
| UB fraction 5 | 84.8 |
| UB fraction 6 | 121.5 |
| Second Capsule Filtration | |
| Loading material | 74.9 |
| UB fraction 1 | 0.3 |
| UB fraction 2 | 0.0 |
| UB fraction 3 | 0.0 |
| UB fraction 4 | 2.1 |
| UB fraction 5 | 0.0 |
| UB fraction 6 | 0.0 |

It was observed that carrying out a second filtration step resulted in an increased removal of FXIa from the immunoglobulin solution as compared to carrying out a single filtration step. It is also shown the second filtration did not alter the high IgG recovery (a total protein recovery of 91.6% was obtained following the second filtration step).

These results indicate that in order to obtain maximal removal of FXIa from the immunoglobulin solution while substantially preserving the IgG levels, the solution can be subjected to a cation-exchanger more than once.

Example 6

The Efficacy of an Affinity Column Chromatography in Removing FXIa from an Immunoglobulin Solution In Examples 1-5 it was shown that a cation—exchange chromatography was an effective step for removing FXIa from an immunoglobulin solution at a pH range of 3.8 to lower than 6. In the following example, the efficacy of an affinity column chromatography in the removal of FXIa was examined. Benzamidine Sepharose-column (Benzamidine Sepharose binds serine proteases such as FXIa) was used as the affinity column.

For this purpose, an immunoglobulin solution was prepared according to step a-c as described in the Material and Methods section. In the next step, the solution was subjected to the Affinity column. The following conditions were employed in the affinity chromatography: 120 ml solution was loaded to the column; the process was carried out at room temperature (22±2° C.); the pH of the immunoglobulin solution was 7.4; a fluid flow rate of 1.3 ml/min was used; the temperature of the subjected solution was 22±2° C. The column was prepared according to the manufacturer's instructions—5 ml of benzamidine sepharose (GE healthcare Catalog Number 17-5123-01) were mounted inside a 1 cm diameter column (Bio-Rad). Prior to use the column was washed with 5 CV of purified water and equilibrated with 5 CV Buffer (50 mM Citrate and 0.2 M NaCl) having a pH of 7.4.

Three filtrate samples (40 ml per fraction) were collected and FXIa level was measured in the loading material and in the filtrate sample using the fluorogenic method as described above in the Material and Method section. The results are presented in Table 7 below.

TABLE 7

The effect of para-amino benzamidine affinity column chromatography in the removal of FXIa from an immunoglobulin solution.

| Sample | FXIa (ng/ml) Using a fluorogenic method |
|---|---|
| Loading material | 363.9 |
| Un-bound (UB) fraction 1 | 90.6 |
| UB fraction 2 | 267.1 |
| UB fraction 3 | 290.5 |

It was observed that in the first un-bound (UB) fraction the column was capable of effectively binding FXIa. However, in the second and third UB fractions, FXIa was detected at high quantities in the immunoglobulin solution.

These results indicate that under the used condition Benzamidine Sepharose affinity chromatography is not suitable for effectively removing FXIa from an immunoglobulin solution.

In the above experiment it was found that in the tested conditions Benzamidine Sepharose affinity column was not effective in removing FXIa. In the following set of experiments heparin-affinity chromatography was tested (heparin was tested due to its ability to bind FXI and FXIa). In this experiment, the effect of different pH levels of the immunoglobulin solution was evaluated (in the range of 5.3-8).

For this purpose, an immunoglobulin solution was prepared according to steps (a) through (c) described above in the Material and Method section. In the next step, the pH of the solution was adjusted either with 0.5 N NaCl or with 0.1 N NaOH to the desired tested pH and 150 ml of each of the immunoglobulin solutions with different pH were subjected to the heparin-affinity chromatography.

Column's preparation: 8 ml of Capto Heparin resin (GE healthcare) were mounted inside a 1 cm diameter column (Bio-Rad) achieving a bed height of 10 cm. The chromatography was carried out at room temperature (22±2° C.) at a flow rate of 2 ml/min. The temperature of the loaded solution was 22±2° C. The column was equilibrated, prior to loading the immunoglobulin solution, with 40 ml of 50 mM citrate buffer having a pH level corresponding to the pH level of the immunoglobulin solution to be loaded (i.e. a pH level of 5.3, 6.5, 7.4, and 8).

Four filtrate fractions (40 ml per fraction) were collected and FXIa level was evaluated in the loading material and in the filtrate fractions using the fluorogenic method as described above. The results are presented in Table 8 below.

TABLE 8

The effect of heparin- affinity chromatography carried out at different pH levels of an immunoglobulin solution on the efficacy to remove FXIa from the solution.

| pH level of the loading material | Sample | FXIa (ng/ml) Using a fluorogenic method |
|---|---|---|
| 5.3* | Load | 192.87 |
| | Un-bound (UB) fraction 1 | 25.51 |
| | UB fraction 2 | 28.92 |
| | UB fraction 3 | 40.85 |
| | UB fraction 4 | 201.48 |
| 6.5 | Load | 201.8 |
| | Un-bound (UB) fraction 1 | 38.7 |
| | UB fraction 2 | 47.9 |
| | UB fraction 3 | 55.2 |
| | UB fraction 4 | 190.4 |
| 7.4 | Load | 214.2 |
| | UB fraction 1 | 51.0 |
| | UB fraction 2 | 64.6 |
| | UB fraction 3 | 107.0 |
| | UB fraction 4 | 159.6 |
| 8 | Load | 209.9 |
| | UB fraction 1 | 65.4 |
| | UB fraction 2 | 78.7 |
| | UB fraction 3 | 112.7 |
| | UB fraction 4 | 167.0 |

*In pH 5.3 the following conditions were used (instead of the conditions specified for the rest of the pH levels): 8 ml Heparin-Hyper DM (GE Healthcare Life Sciences) was used; and the loading volume was 125 ml. Equilibration prior to loading was carried out with 40 ml buffer (containing 50 mM citrate and 0.2M NaCl at pH 7.4) at a fluid flow rate of 2 ml/min. In general, it was observed that binding of FXIa to the heparin resin improved by decreasing the pH of the immunoglobulin solution. The best results were observed on the first three unbound fractions of the lowest pH (5.3). However, after about 15 column volume, FXIa is collected in the filtrate (relatively high FXIa quantity in UB fractions 4 of pH 5.3 was observed).

Example 7

The Effect of pH Level of an Immunoglobulin Solution on Efficacy of an Anion-exchange Chromatography to Remove PKA from the Solution The following experiment was aimed to determine the effect of the pH level of an immunoglobulin solution on PKA removal from the solution by an anion-exchanger.

In this experiment the effect of a pH level range of 6.4-8.2 was evaluated. The pH level of the solution was measured using an electronic pH monitoring device.

DEAE-column (Toyopearl DEAE-650M; TOSOHAAS) was used as the anion-exchanger. 11 ml resin was used. The column's diameter was 1 cm, and a bed height of 14 cm was used.

In this experiment an immunoglobulin solution prepared from paste II and subjected to CUNO filtration in the manner described in the Materials and Methods section (an immunoglobulin solution following step b) was used. In the next step, the pH level of the solution was adjusted with 0.5 N HCl or 0.5 N NaOH to the desired tested pH level (a pH range of 6.4-8.2) and 200 ml of each of the resulting immunoglobulin solutions was subjected to the anion-exchange chromatography (step c of the immunoglobulin solution preparation described in the Materials and Methods section) (in all experiments, 200 ml containing about 70 mg/ml protein were subjected to the anion-exchange chromatography). The chromatography step was carried out at 8° C.; the temperature of the loaded immunoglobulin solution was 8° C.; and a linear fluid flow rate of 1.65 ml/min/cm$^2$ was used.

In Example 7 through 11, the same immunoglobulin solution was used as the loading material ("Load"), i.e. the PKA level of the loading material was identical in all experiments.

The level of PKA and other characteristics of the immunoglobulin solution such as the total protein recovery, IgG subclasses distribution, the titer levels of anti-HBsAg and Anti-Diphtheria Antibodies were evaluated in the "unbound" fraction (=after subjecting the solutions to the anion exchanger). The evaluations were carried out as described in the Materials and Methods section. The results are summarized in Table 9.

TABLE 9

The effect of pH level of an immunoglobulin solution on the efficacy of DEAE-column to remove PKA.

| pH level of the loading material | Total protein Recovery** (%) | Anti-HBsAg (mIU/ml) | PKA (IU/ml) | IgG subclasses distribution (%) | | | | Anti-Diphtheria Antibodies (IU/ml) |
|---|---|---|---|---|---|---|---|---|
| | | | | IgG1 | IgG2 | IgG3 | IgG4 | |
| 6.4 | 97 | 4762 | 14.4 | ND | ND | ND | ND | ND |
| 7.0 | 97 | 4884 | <LOQ | 62.9 | 29.5 | 6.7 | 0.9 | 6.1 |
| 7.6 | 95 | 3450 | <LOQ | 63.6 | 28.8 | 6.6 | 1.0 | 5.8 |
| 8.2 | 97 | 2481 | <LOQ | 64.7 | 28.7 | 5.7 | 0.9 | 5.3 |

* ND—Not Determined; LOQ—limit of quantitation - a value of <6.
**Total protein recovery (%) was calculated by comparing the protein content (using the Biuret method) before and after subjecting the solution to the column.

It was observed that a low pH level of 6.4 resulted in an increased PKA content in the recovered IgG solution as compared to the higher pH levels. It was also observed that a pH level in the range of 7-8.2 (a range wherein the PKA has a zero net electrical charge and as such is not expected to bind to positively charged groups) resulted in an increased capacity of the anion-exchanger to remove PKA (the PKA level was below the limit of quantitation). The results also show that a pH level range of 7-8.2 also resulted in high protein recoveries in the un-bound fraction (a pH level wherein the IgG has a net zero or negative charge and it was expected that some of it would be bound to the anion exchanger) (protein recoveries in the range of 95-100% were obtained), in unaltered IgG subclass distribution characteristics [typical IgG subclasses distribution (IgG1—about 65%, IgG2—about 30%, IgG3—about 6%, and IgG4—about 1%), and typical anti-HBsAg (in the range of 2000-5000 mIU/ml) and anti-Diphtheria antibody titres (about 6 IU/ml)].

These results indicate that the immunoglobulin solution should have a pH level range of 7 to 8.2 while subjected to the anion-exchanger in order to efficiently remove PKA from the solution.

Example 8

The Effect of Temperature Level on PKA Removal from an Immunoglobulin Solution by Anion-exchange Chromatography The following experiment examines the effect of temperature level of an immunoglobulin solution on PKA removal from the solution by an anion-exchanger. Immunoglobulin solutions equilibrated to the following temperatures were evaluated: 2, 8, 14 and 20° C. The starting immunoglobulin solution (loading material) used and a DEAE-column were used as in Example 7. The chromatography step itself was carried out at 8° C.; a linear fluid flow rate of 1.65 ml/min/cm$^2$ and a pH level of 7.5 were used; and the loading volume was 200 ml.

The level of PKA and other characteristics of the immunoglobulin solution (same parameters as above) were evaluated in the un-bound fraction. The results are summarized in Table 10.

TABLE 10

The effect of the temperature of an immunoglobulin solution on the efficacy of DEAE-column to remove PKA.

| Temperature level of the loading material (° C.) | Total protein recovery (%) | PKA (IU/ml) | Anti-HBsAg (mIU/ml) | IgG subclasses distribution (%) | | | | Anti-Diphtheria Antibodies (IU/ml) |
|---|---|---|---|---|---|---|---|---|
| | | | | IgG1 | IgG2 | IgG3 | IgG4 | |
| 2 | 100 | 7.7 | 4616 | ND | ND | ND | ND | ND |
| 8 | 96 | <LOQ | 3222 | 65.4 | 27.0 | 6.5 | 1.1 | 6.4 |
| 14 | 97 | <LOQ | 3620 | 65.0 | 27.8 | 6.3 | 1.0 | 6.4 |
| 20 | 100 | <LOQ | 4970 | 64.1 | 27.8 | 7.0 | 1.1 | 6.4 |

* ND—not determined; LOQ—limit of quantitation - a value of <6.

It was found that an IgG solution loaded having a low temperature of 2° C. resulted in an increased PKA content in the recovered unbound fraction. A temperature in the range of 8 to 20° C. resulted in an optimal PKA removal (the PKA level was below the limit of quantitation), with unaltered IgG content and IgG subclass distribution characteristics following the DEAE chromatography step, and typical anti-HBsAg and anti-Diphtheria antibody titres (see typical values above).

Example 9

The Effect of the Loading Volume of an Immunoglobulin Solution on Efficacy of an Anion-exchange Chromatography to Remove PKA The following experiment examines the effect of the loading volume of an immunoglobulin solution on PKA removal from the solution by an anion-exchanger. The following volumes were loaded onto the column: 12 column volume (CV), 20 CV, and 25 CV (the resin's volume and the column's premasters are as in Example 7). By "12 column volume" it is meant 12 times the resin's volume (which was 11 ml).

The starting immunoglobulin solution (loading material) used was as in Example 7 and a DEAE-column was used as the anion-exchanger. The chromatography step was carried out at 8° C.; according to the preceding Examples, the temperature of the loaded immunoglobulin solution was 8° C. and the pH was 7.5; and a linear fluid flow rate of 1.65 ml/min/cm$^2$ was used.

The level of PKA and other characteristics of the immunoglobulin solution (same parameters as above) were evaluated in the un-bound fraction. The results are summarized in Table 11.

TABLE 11

The effect of increasing loading volumes of an immunoglobulin solution on the efficacy of a DEAE-column to remove PKA.

| Load volume (CV) | Total protein recovery (%) | PKA (IU/ml) | Anti-HBsAg (mIU/ml) | IgG subclasses distribution (%) | | | | Anti-Diphtheria (IU/ml) |
|---|---|---|---|---|---|---|---|---|
| | | | | IgG1 | IgG2 | IgG3 | IgG4 | |
| 12 | 100 | <LOQ | 5107 | 63.2 | 29.2 | 6.6 | 1.0 | 6.5 |
| 20 | 93 | <LOQ | 3727 | 64.8 | 27.9 | 6.4 | 0.9 | 6.4 |
| 25 | 99 | <LOQ | 5329 | 66.6 | 26.0 | 6.4 | 1.1 | 6.1 |

* LOQ—limit of quantitation - a value of <6.

The results show that in all tested loading volumes the DEAE-column efficiently removed PKA substantially without impairing protein recoveries (a total protein recovery in the range of 93-100% were obtained), IgG characteristics (all the values are comparable to the typical values or anti-Diphtheria and Anti-HBsAg titers (see the typical values in the Example 7).

Example 10

The Effect of the Linear Velocity of the Immunoglobulin Solution During Subjection to an Anion-exchange Chromatography on Efficacy of the Chromatography to Remove PKA The following example examines the effect of linear velocity of the solution during loading on the efficacy of the anion-exchange chromatography to remove PKA. The following linear velocities were evaluated: 1, 2, 3, and 4 cm/min/ml.

The loading material used and the DEAE-column used were as in Example 7. The chromatography step was carried out at 8° C.; the temperature of the loaded immunoglobulin solution was 8° C.; a pH of 7.5 was used; and the loading volume was 200 ml.

The level of PKA and other characteristics of the immunoglobulin solution (same as above) were evaluated in the un-bound material. The results are summarized in Table 12.

TABLE 12

The effect of linear velocity of an immunoglobulin solution on the efficacy of a DEAE-column to remove PKA.

| Linear velocity of the loading material (cm/min/ml) | Total Protein Recovery (%) | Anti-HBsAg (mIU/ml) | PKA (IU/ml) | IgG subclasses distribution (%) | | | | Anti-Diphtheria Antibodies (IU/ml) |
|---|---|---|---|---|---|---|---|---|
| | | | | IgG1 | IgG2 | IgG3 | IgG4 | |
| 1 | 97 | 3870 | <LOQ | 65.5 | 27.4 | 6.1 | 1.0 | 5.3 |
| 2 | 96 | 3844 | <LOQ | 65.5 | 27.0 | 6.4 | 1.1 | 5.2 |
| 3 | 98 | 3739 | 11.2 | ND | ND | ND | ND | ND |
| 4 | 101 | 3751 | 8.6 | ND | ND | ND | ND | ND |

* ND—not determined; LOQ—limit of quantitation - a value of <6.

The results show that a linear velocity between 1 and 2 cm/min/ml efficiently removed PKA from the immunoglobulin solution without impairing protein recovery or IgG characteristics. Higher linear velocities (e.g. 3-4 cm/min/ml) resulted in lower PKA removal.

Example 11

Removal of Thrombogenic Agents from an Immunoglobulin Solution by Using Tandem Ion-exchange Chromatography An immunoglobulin solution was prepared from paste II and subjected to CUNO filtration in the manner described in the Materials and Methods section (an immunoglobulin solution following step b). In the next step, the solution was subjected to a DEAE-column [(Toyopearl DEAE-650M; TOSOHAAS) (11 ml resin was used; the column's diameter was 1 cm, and a bed height of 14 cm was used)] under the following conditions: the chromatography step was carried out at 8° C.; the temperature of the loaded immunoglobulin solution was 8° C.; a linear fluid flow rate of 1.65 ml/min/cm$^2$; and the pH level of the loaded immunoglobulin solution was equilibrated to 7.5. The volume of the loaded solution was 200 ml. The column was equilibrated prior to loading the solution as described in the Materials and Methods section.

The level of PKA and other characteristics of the immunoglobulin solution (as above) were evaluated in the "unbound" fraction (=after subjecting the solutions to the anion exchanger). The measurements were carried out as described in the Materials and Methods section. The results are summarized in Table 13.

TABLE 13

PKA removal from an immunoglobulin solution by an anion-exchanger.

| PKA (IU/ml) | Total Protein Recoveries (%) | Anti-HBsAg (mIU/ml) | IgG subclasses (%) | | | | Anti-Diphtheria (IU/ml)* |
|---|---|---|---|---|---|---|---|
| | | | IgG1 | IgG2 | IgG3 | IgG4 | |
| <LOQ | 100 | 4332 | 63.6 | 28.9 | 6.6 | 0.9 | 6.7 |

LOQ—limit of quantitation - a value of <6.

The results show that under the used conditions, the DEAE-column efficiently removed PKA substantially without impairing protein recovery (a total protein recovery of 100 was obtained), IgG characteristics (all the values are comparable to the typical values), anti-Diphtheria and anti-HBsAg titers (see the typical values in the Example 7).

Following contacting the immunoglobulin solution with the anion-exchanger, the collected un-bound fraction is subjected to steps d)-e) of the immunoglobulin preparation as described in the Material and Methods section. In the next step, the solution is subjected to a cation exchanger under the following conditions: a pH level in the range of 3.8 to 6; a flow rate of lower than 2.5 ml/min [e.g. a flow rate in the range of 0.7 to 1.5 ml/min (2-4.3 MV/min)]; and the temperature of the loaded immunoglobulin composition is in the range of from room temperature (22±2° C.) down to 7° C.

FXIa removal is evaluated in the loading material ("Load") and after collecting the solution from the column ("Un-bound"). The measurement is carried out by the TG assay and/or by the fluorogenic method as described in the Materials and Methods section.

Example 12

The Effect of SDR-column on FXIa Removal from an Immunoglobulin Solution

The following experiment was aimed to determine the ability of SDR-column to remove FXIa from an immunoglobulin solution.

For this purpose, an immunoglobulin solution was prepared from paste II according to step a)-e) in the manner described in the Materials and Methods section. In the next step, the solution was subject to a cation-exchange chromatography using Mustang® S capsule as follows (scale-up conditions):

Prior to subjecting the immunoglobulin solution to the cation-exchanger, the solution was filtered through 0.2 μm CA filter obtained from Corning (in order to reduce aggregates). The Mustang® filtration was carried out through two Mustang® S filters which were connected in series. Prior to the Mustang® filtration, the two filters were washed separately with 30 Kg of 1 N NaOH at a flow rate of 2.1 L/min (for both filters). As a second wash, both filters were washed separately with 50 Kg of 1 N NaCl at a flow rate of 1.8 L/min (for the first filter) or at a flow rate of 2.1 L/min (for the second filter). Finally, the filters were washed separately with 50 Kg of 20 mM Sodium Acetate (at a pH of 4.2) at a flow rate of 1.8 L/min (for the first filter) or at a flow rate of 1.9 L/min (for the second filter). The above washes were carried out to obtain a pH level of 4.2. All washes were carried out at a pressure of 0.

Mustang® filtration: the immunoglobulin solution was filtered through the two washed Mustang® S filters at a flow rate of 1.6 L/min. A total of 160 Kg immunoglobulin solution (un-bound fraction) was collected. The temperature of the loaded solution was 7° C. while the filter was at room temperature. The pH of the loaded immunoglobulin solution was 4.2-4.3.

In the next step, the filtrate (un-bound fraction) was subjected to Solvent/Detergent (S/D) treatment and SDR-column as described in the Materials and Methods section.

The level of FXIa was measured in the solution before filtering the solution through the Mustang S membrane (i.e. an immunoglobulin solution prepared according to step a-e as described in the Material and Methods section), after filtering the solution through the Mustang S membrane, and after subjecting the solutions to S/D treatment+SDR-column.

The evaluation was carried out by a fluorogenic method as described in the Materials and Methods section. The results are presented in Table 14 below.

TABLE 14

Removal of FXIa from an immunoglobulin solution by SDR-column.

| Tested sample | FXIa (ng/ml) Using a fluorogenic method |
|---|---|
| Pre-Mustang S filtration | 529.4 |
| Post-Mustang S filtration | 37.6 |
| Post SD treatment + SDR-column | 3.9 (<LOD) |

* LOD—limit of detection.

As shown in Table 14, the addition of S/D treatment and S/D removal step by SDR-column results in removal of residual amounts of FXIa.

Example 13

Removal of Kallikrein from an Immunoglobulin Solution by Using Mustang® S Capsule (a Cation-exchanger)

The following experiment was aimed to determine the ability of Mustang® capsule to remove kallikrein from an immunoglobulin solution.

For this purpose, an immunoglobulin solution was prepared from paste II according to steps (a)-(e) in the manner described in the Materials and Methods section. In the next step, the solution was subject to the Mustang® S capsule as follows (scale-up conditions):

Prior to the Mustang® filtration, each filter was pre-washed separately with at least 30 Kg of 1 N NaOH at a flow rate of 1.6-2.3 L/min. As a second wash, each filter was washed separately with at least 50 Kg of 1 N NaCl at a flow rate of 1.6-2.3 L/min. Finally, each filter was equilibrated separately with 50 Kg of 20 mM Sodium Acetate (at a pH of 4.2) at a flow rate of 1.6-2.3 L/min. The above washes were carried out to obtain a pH level of 4.2. All washes were carried out at a pressure of ≤1 bar.

Prior to subjecting the immunoglobulin solution to the cation-exchanger, the solution was filtered through 0.2 μm Durapore filter (Milipore) (in order to reduce aggregates). The resulting immunoglobulin solution was filtered through two Mustang® S capsules (which were pre-washed and equilibrated as specified above) that were connected in series.

Mustang® filtration: the immunoglobulin solution was filtered through the two capsules at a flow rate of 1.6-2.3 L/min [about 160 Kg (about 160 L) immunoglobulin solution was loaded; and about 70 mg/ml protein]. A total of about 160 Kg immunoglobulin solution (about 160 L) (un-bound fraction) was collected.

The temperature of the loaded solution was about 7° C. while the filter was at room temperature; filtration was carried out at RT; the pH of the loaded immunoglobulin solution was 4.1-4.3.

The level of Kallikrein removal was measured in the immunoglobulin solution before ("Pre-filtration") and after filtration ("Post-filtration") through the Mustang® S capsule, and the percentage of Kallikrein removal was calculated. The evaluation was carried out by a chromogenic method as described in the Materials and Methods section.

To estimate the IgG recovery after filtration, the total protein recovery (%) was measured The obtained Kallikrein removal is shown in Table 15 below, and the obtained total protein recovery (%) is shown in Table 16.

TABLE 15

Kallikrein removal by Mustang ® S filters.

| Sample | $V_{max}$* | Kallikrein (ng/ml) | Removal (%) |
| --- | --- | --- | --- |
| Pre-filtration | 478.2 | 3760.6 | |
| Post-filtration | 20.6 | 126.1 | 97% |

TABLE 16

Protein recovery following Mustang ® S filtration.

| Sample | Total protein (mg/ml) | Protein Recovery (%) |
| --- | --- | --- |
| Pre-filtration | 65.4 | |
| Post-filtration | 63.4 | 97% |

It was observed that under the specified conditions, loading an immunoglobulin solution to a cation exchanger resulted in 97% kallikrein removal while 97% of the protein (IgG) was recovered.

Example 14

Checking the Thrombosis-inducing Activity of an Immunoglobulin Solution Prepared According to the Invention in an In-vivo Model The following experiment was aimed to examine whether an immunoglobulin solution which was subjected to kallikrein, PKA and/or FXIa removal as in the preceding Examples exhibit reduced thrombosis-inducing activity. The evaluation was carried out using an in-vivo model as described in Wessler et al. (Biologic assay of a thrombosis-inducing activity in human serum. J Appl Physiol. 1959; 14:943-946).

It was observed, using the Wessler animal model, that an immunoglobulin solution subjected to PKA and/or FXIa removal according to the invention exhibited reduced thrombosis-inducing activity.

The invention claimed is:

1. A method for removing thrombogenic agents selected from the group consisting of prekallikrein activator (PKA) and Factor XIa; PKA and Factor XI; PKA Factor XIa, and Kallikrein; PKA, Factor XI and Kallikrein; and PKA, Factor XIa, Factor XI and Kallikrein from an immunoglobulin containing solution, the method comprising the steps of: contacting the solution with a support comprising immobilized negatively charged groups equilibrated at a pH in the range of higher than 3.8 to equal to or lower than 5.3 and with a support comprising immobilized positively charged groups equilibrated at a pH in the range of 7.0 to 8.2 to allow PKA binding to the positively charged groups and Factor XIa, Factor XI and/or Kallikrein binding to the negatively charged groups; and collecting unbound fractions comprising immunoglobulin.

2. The method according to claim 1, wherein the negatively charged groups are equilibrated at a pH in the range of higher than 3.8 to equal to or lower than 5.0.

3. The method according to claim 1, wherein the negatively charged groups are equilibrated at a pH in the range of equal to or higher than 4.0 to equal to or lower than 5.0.

4. The method according to claim 1, wherein the negatively charged groups are equilibrated at a pH in the range of higher than 3.8 to equal to or lower than 4.7.

5. The method according to claim 1, wherein the negatively charged groups are equilibrated at a pH of about 4.0, 4.1, 4.2, 4.3, 4.4, 4.5, 4.6, or 4.7.

6. The method according to claim 1, wherein the negatively charged groups are equilibrated at a pH in the range of higher than 3.8 to equal to or lower than 4.3.

7. The method according to claim 1, wherein the negatively charged groups are equilibrated at a pH in the range of equal to or higher than 4.0 to equal to or lower than 4.3.

8. The method according to claim 1, wherein the negatively charged groups are equilibrated at a pH in the range of equal to or higher than 4.1 to equal to or lower than 4.3.

9. The method according to claim 1, wherein the support comprising immobilized negatively charged groups and/or the support comprising immobilized positively charged groups are in the form of a chromatographic material or a chromatographic membrane.

10. The method according to claim 1, wherein the charged groups are immobilized to the support via a linker present between the support and the charged groups.

11. The method according to claim 10, wherein the linker is selected from the group consisting of a protein, amino acid and peptide.

12. The method according to claim 1, wherein the support comprising immobilized negatively charged groups and/or the support comprising immobilized positively charged group are chemically modified.

13. The method according to claim 1, wherein the immobilized negatively charged groups are selected from the group consisting of derivatives of sulfonic and other sulfur containing acids, formic and other carboxylic acids, phosphoric and other phosphorous containing acids, nitrate and other nitrogen containing acids, and a combination thereof.

14. The method according to claim 13, wherein the immobilized negatively charged groups are sulfur containing acids.

15. The method according to claim 14, wherein the sulfur containing acids are sulfopropyl.

16. The method according to claim 13, wherein the immobilized negatively charged groups are carboxylic acids.

17. The method according to claim 16, wherein the carboxylic acids are carboxymethyl.

18. The method according to claim 1, wherein the immobilized positively charged groups are selected from the group consisting of ammonium, alkyl ammonium, dialkylammonium, trialkyl ammonium, quaternary ammonium, alkyl groups, H+, Na+, K+, Ca2+, Mg2+, amino functional group, and a combination thereof.

19. The method according to claim 18, wherein the immobilized positively charged groups are quaternary ammonium.

20. The method according to claim 19, wherein the quaternary ammonium is Diethylaminoethyl (DEAE).

21. The method according to claim 1, wherein contacting the solution with the support comprising the positively charged groups is carried out at a linear velocity in the range of 1 to 2 ml/min/cm2, and wherein the immunoglobulin containing solution has a temperature in the range of 2 to 22° C.

22. The method according to claim 1, further comprising the steps of: contacting the solution, prior to contacting with the support comprising immobilized negatively charged groups, with a chromatographic material comprising three-dimensional cross-linked hydrophobic acrylic polymer.

* * * * *